(12) United States Patent
Kim et al.

(10) Patent No.: US 11,000,501 B2
(45) Date of Patent: May 11, 2021

(54) COMPOSITION FOR PREVENTING OR TREATING NEUROLOGICAL AND MENTAL DISORDERS, CONTAINING SYRINGARESINOL

(71) Applicant: SEOUL NATIONAL UNIVERSITY R&DB FOUNDATION, Seoul (KR)

(72) Inventors: Myoung Hwan Kim, Seoul (KR); Young Seon Cho, Seoul (KR); Woo Seok Song, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 208 days.

(21) Appl. No.: 16/343,724

(22) PCT Filed: Oct. 19, 2017

(86) PCT No.: PCT/KR2017/011596
§ 371 (c)(1),
(2) Date: Oct. 9, 2019

(87) PCT Pub. No.: WO2018/074863
PCT Pub. Date: Apr. 26, 2018

(65) Prior Publication Data
US 2020/0038363 A1    Feb. 6, 2020

(30) Foreign Application Priority Data

Oct. 19, 2016 (KR) .................. 10-2016-0135964

(51) Int. Cl.
| | |
|---|---|
| A61K 31/34 | (2006.01) |
| A61P 25/28 | (2006.01) |
| A61P 25/30 | (2006.01) |
| A61P 25/18 | (2006.01) |
| A61P 25/24 | (2006.01) |
| A61P 25/08 | (2006.01) |
| A61P 35/00 | (2006.01) |

(52) U.S. Cl.
CPC .............. *A61K 31/34* (2013.01); *A61P 25/08* (2018.01); *A61P 25/18* (2018.01); *A61P 25/24* (2018.01); *A61P 25/28* (2018.01); *A61P 25/30* (2018.01); *A61P 35/00* (2018.01)

(58) Field of Classification Search
CPC ..................................................... A61K 31/34
USPC ......................................................... 514/469
See application file for complete search history.

(56) References Cited

FOREIGN PATENT DOCUMENTS

| | | |
|---|---|---|
| KR | 10-0853439 B1 | 8/2008 |
| KR | 10-2012-0119227 A | 10/2012 |
| KR | 10-2014-0070176 A | 6/2014 |
| KR | 10-2015-0092038 A | 8/2015 |
| KR | 10-2015-0111073 A | 10/2015 |

OTHER PUBLICATIONS

PCT/KR2017/011596, International Search Report and Written Opinion (with English Translation), 27 pages, dated Jan. 25, 2018.

*Primary Examiner* — Jeffrey H Murray
(74) *Attorney, Agent, or Firm* — Stoel Rives LLP; Kelly A. Echols

(57) ABSTRACT

The present invention relates to a pharmaceutical composition for prevention or treatment of neurological diseases and mental diseases, the composition containing syringaresinol. The syringaresinol according to the present invention has an effect of reducing excitatory synaptic transmission in a central nervous system and an effect of suppressing epilepsy and activity of animals. This suppressive effect of the excitatory synaptic transmission may be effectively used for the prevention and treatment of all neurological diseases and mental diseases resulting from synapse dysfunction and synpatic excitatory-inhibitory transmission imbalance.

5 Claims, 20 Drawing Sheets

COMPOSITION FOR PREVENTING OR TREATING NEUROLOGICAL AND MENTAL DISORDERS, CONTAINING SYRINGARESINOL

RELATED APPLICATIONS

This application is a United States National Phase entry of International Application No. PCT/KR2017/011596, filed Oct. 19, 2017, which claims the benefit of the Republic of Korea Application No. 10-2016-0135964, filed Oct. 19, 2016. The entire contents of each of the foregoing applications are hereby incorporated by reference herein.

TECHNICAL FIELD

The present invention relates to a pharmaceutical composition for prevention or treatment of neurological diseases and mental diseases, the composition containing syringaresinol.

BACKGROUND ART

Excitatory synaptic transmission plays an important role in communication between neurons in the central nervous system. In mammals, most of excitatory synaptic transmission is accomplished when postsynaptic AMPA receptor (AMPAR) and NMDA receptor (NMDAR) are open in response to glutamate released from a presynaptic terminal.

The AMPA and NMDA receptors are ligand gated ion channels whose gating is controlled by glutamate secreted from the presynaptic terminal. The cell membrane potential is depolarized by permeating cations through the receptors.

The AMPA and NMDA receptor dysfunctions are associated with most of neurological diseases and mental disorders such as hyperactivity, attention deficit, autism, post-traumatic stress disorder (PTSD), intelligence disorder, epilepsy, pain, drug addiction, schizophrenia, obsessive-compulsive disorder, and motor function disorder. Thus, treatment of various neurological diseases and mental diseases via restoration of the AMPA or NMDA receptor function has been attempted. However, no excitatory synapse receptor modulating drugs that effectively permeate a blood brain barrier and is safe for the human body have been developed, so far.

Syringaresinol is also known as lirioresinol B. Syringaresinol is known to have following actions: vascular relaxation via increase in NO (nitric oxide) in a body (Chung et al., 2012), suppression of myocardial damage and death via destabilization of HIF-1a during hypoxia/reoxygenation (Cho et al., 2015), and decrease in motility of *Helicobacter pylori* (Miyazawa et al., 2006).

Further, syringaresinol has been reported to increase expression of intracellular SIRT1 (silent information regulator two ortholog 1) genes in terms of molecules (Cho et al., 2013).

Previously claimed or allowed patent documents relating to the use of the syringaresinol may include followings: inhibition of vascular aging (US20140248381), treatment and prevention of heart disease (20150283110), skin improvement (EP 2772255 A1), activation of SIRT 1 (20140371307), and increasing of a lifespan (PCT/KR2014/002892).

However, there is not reported an effect of the syringaresinol on neuronal and central nervous system. Further, use of the syringaresinol for treatment and prevention of neurological diseases and mental diseases has not been reported.

DISCLOSURE

Technical Problem

Previous studies have attempted to treat various neurological diseases and mental diseases via functional restoration of excitatory synapse. However, an excitatory synapse control drug that effectively permeates a blood brain barrier and is safe for the human body has not been developed.

It is an object of the present invention to provide a novel excitatory synapse function modulating drug which may be used for the prevention or treatment of neurological diseases and mental diseases.

Technical Solution

As the results of the researches in order to solve the above objects, the present inventors have found that the syringaresinol can regulate excitatory synaptic transmission. Thus, the present invention has been completed. Solutions for achieving the object of the present invention are as follows.

1. A pharmaceutical composition for prevention or treatment of a neurological disease or mental disease, the composition comprising a compound represented by the following Chemical Formula 1 or a pharmaceutically acceptable salt thereof:

[Chemical Formula 1]

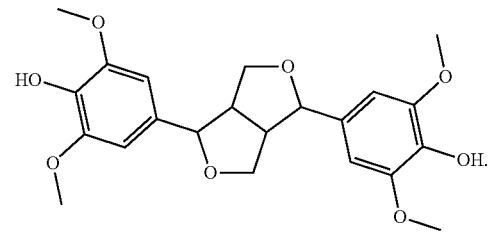

2. A composition for controlling excitatory synaptic transmission, the composition comprising a compound of the Chemical Formula 1 or a pharmaceutically acceptable salt thereof.

3. A food composition for prevention of neurological disease or mental disease, the composition comprising a compound of the Chemical Formula 1 or a pharmaceutically acceptable salt thereof

[Advantageous Effects]

The syringaresinol according to the present invention has the effect of reducing the synaptic transmission through the excitatory synapse receptors (AMPA receptors and NMDA receptors) in the central nerves, and has the effect of reducing animal activity. This inhibitory effect of the excitatory synaptic transmission occurs by affecting secretion of excitatory neurotransmitter from the presynaptic terminal. The regulation of excitatory neurotransmitter secretion by the syringaresinol may be used effectively for treatment and prevention of all neurological and mental diseases associated with synapse excitation-inhibition imbalance, dysfunction of the AMPA and NMDA receptors, and dysfunction of metabotropic glutamate receptors.

DESCRIPTION OF DRAWINGS

FIG. 1 shows that SYR inhibits excitatory synaptic transmission. More specifically.

FIG. 2 shows that SYR does not affect inhibitory synapse transmission in CA1 neurons. More specifically.

FIG. 3 shows that SYR does not affect AMRAR transmission and desensitization. More specifically, FIG. 3F (a lower drawing) shows the EPSC normalized with each peak amplitude.

FIG. 5 shows that the SYR decreases a readily releasable pool (RRP) size. More specifically.

FIG. 6 shows that SYR affects $Ca^{2+}$ current conductance and resting membrane potential. More specifically.

FIG. 7 shows that SYR inhibits picrotoxin-induced epilepsy in the hippocampus. More specifically.

FIG. 8 shows the result of comparing the movement distances of the experimental group and control over time.

MODES OF THE INVENTION

Figure 1A:
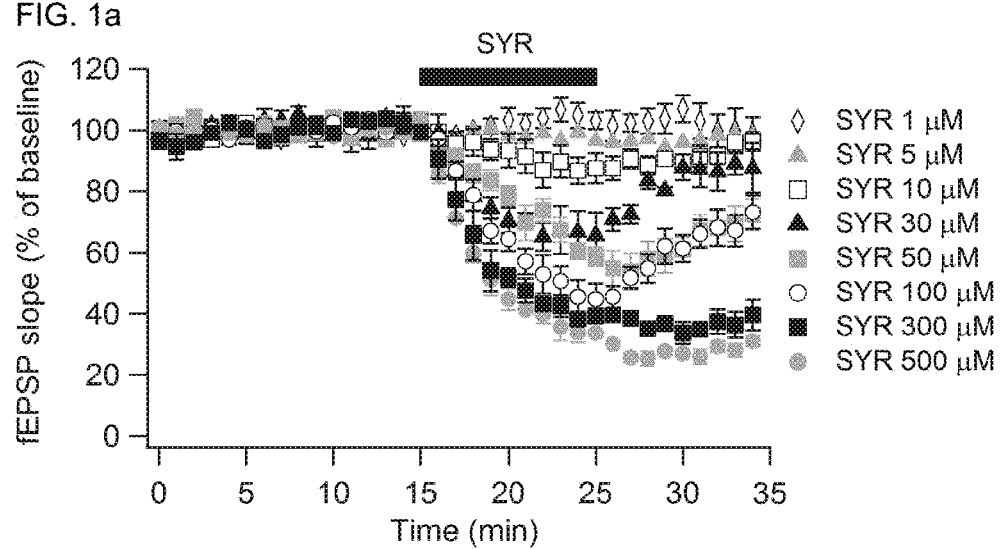
FIG. 1A shows that SYR inhibits a slope of fEPSP of SC-CA1 synapse in a dose-dependent manner.

The present invention provides a pharmaceutical composition for the prevention or treatment of a neurological disease or mental disease, the composition comprising a compound represented by a following Chemical Formula 1 or a pharmaceutically acceptable salt thereof:

[Chemical Formula 1]

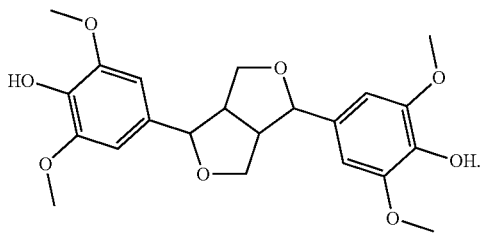

The compound of the Chemical Formula 1 may be called syringaresinol and may also be referred to as lirioresinol B. Syringaresinol is a lignan found in plants such as *Acanthopanax divaricatus*, *Prunus mume*, *Magnolia thailandica*, and *Castela emoryi* belong to Quassia Family, and has a molecular weight of 418.43 g/mol.

The syringaresinol may reduce synapse transmission and animal activity through the AMPA and NMDA receptors in the central nervous system. The inhibitory effect of syringaresinol on the excitatory synaptic transmission may be effectively used for the prevention and treatment of all neurological and mental diseases associated with dysfunction of AMPA and NMDA receptors.

The neurological disease for which the pharmaceutical composition of the present invention may be used may include brain tumor, cerebral infarction, hypertensive cerebral hemorrhage, cerebral contusion, cerebral arteriovenous malformation, brain abscess, encephalitis, hydrocephalus, epilepsy, concussion, cerebral palsy, dementia, spinal cord tumor, spinal arteriovenous malformation and spinal cord infarction. The pharmaceutical composition of the present invention may be also used for other neurological diseases related to excitatory synapse dysfunction or synapse excitation-inhibition imbalance.

Mental diseases for which the pharmaceutical composition of the present invention may be used are selected from the group consisting of hyperactivity, attention deficit, autism, posttraumatic stress disorder (PTSD), intelligence disorder, dementia, drug addiction, schizophrenia, obsessive-compulsive disorder, delusion of grandeur, character disorder, neuropathy, alcoholism, enuresis, manic depression and motor function disorder. The pharmaceutical composition of the present invention may be also used for other mental diseases related to the excitatory synapse dysfunctions or synapse excitatory-inhibition imbalance.

As used herein, the pharmaceutical composition may further comprise at least one of a pharmaceutically acceptable carrier, excipient and diluent. The carrier, excipient and diluent which may be used include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate, and mineral oil.

When the pharmaceutical composition of the present invention is formulated, the formulation may contain commonly used fillers, extenders, binders, wetting agents, disintegrating agents, surfactants and the like. Solid formulations for oral administration include tablets, pills, powders, granules, capsules, and the like. Such a solid preparation may be prepared by mixing at least one excipient such as starch, calcium carbonate, sucrose or lactose, gelatin and the like with the extract. Further, in addition to simple excipients, lubricants such as magnesium stearate and talc may also be used. Liquid preparations for oral administration include suspensions, solutions, emulsions and syrups. In addition to commonly used simple diluents such as water and liquid paraffin, various excipients such as wetting agents, sweeteners, fragrances, preservatives and the like may be included in the formulation. Formulations for parenteral administration include sterilized aqueous solutions, non-aqueous solutions, suspensions, emulsions, freeze-dried preparations, and suppositories. Examples of the non-aqueous solutions and suspensions include propylene glycol, polyethylene glycol, vegetable oil such as olive oil, injectable ester such as ethyl oleate, and the like. A suppository base may include witepsol, macrogol, tween 61, cacao butter, laurinum, glycerogelatin and the like.

The pharmaceutical composition of the present invention is administered in a pharmaceutically effective amount.

As used herein, the term "pharmaceutically effective amount" means an amount as sufficient to treat a disease but as low to avoid a risk. Specific values thereof may depend on factors well known in the art and other medical fields including the type and severity of the subject to be administered, age, sex of the subject, drug activity, drug sensitivity of the subject, time of administration, route of administration and rate of release of the drug, duration of treatment of the subject, and co-administered drug.

Further, the pharmaceutical composition of the present invention may be used in combination with other conventional drugs used for the treatment or prevention of neurological disease or mental disease. When the pharmaceutical composition of the present invention is used in combination with other conventional drugs, the pharmaceutical composition of the present invention and the other drugs may be administered sequentially or simultaneously. The administration order may be easily determined by a person skilled in the art.

The route of administration of the pharmaceutical composition of the present invention may be determined as any conventional route so long as the composition can reach a target tissue along the route. The composition of the present invention may be administered intraperitoneally, intravenously, intramuscularly, subcutaneously, intradermally, orally, nasally, intrapulmonarily or intrarectally, as desired. The present invention is not limited thereto. Further, the composition may be administered by any device by which the active substance may migrate to the target cell.

As used herein, a term "treatment" includes not only cure of the disease, but also partial cure, improvement and alleviation of the symptom.

As used herein, a term "prevention" means suppressing occurrence of the disease before the disease occurs or finding the disease early and treating it in a timely manner.

Further, the present invention provides a composition for controlling excitatory synaptic transmission, the composition comprising a compound represented by the Chemical Formula 1 or a pharmaceutically acceptable salt thereof.

Since the syringaresinol of the present invention can regulate the synaptic transmission through the AMPA receptor and the NMDA receptor without significantly affecting the inhibitory synapse function, the syringaresinol of the present invention may also be used for the composition for the control of the synapse excitation-inhibition imbalance.

The syringaresinol of the present invention suppresses the secretion of excitatory neurotransmitter from the presynaptic terminal, and thus may be used for the composition for regulating neurotransmitter secretion.

Further, syringaresinol affects the secretion of neurotransmitters and thus may be used for a composition to control cellular signaling through metabotropic glutamate receptors and through Kaimate receptors.

Further, the present invention provides a food composition for the prevention of neurological disease or mental disease, the composition comprising the compound represented by the Chemical Formula 1 or a pharmaceutically acceptable salt thereof.

The food composition may further comprise ingredients normally added in the manufacture of the food, for example, proteins, carbohydrates, fats, nutrients, condiments and flavoring agents.

Examples of such carbohydrates may include monosaccharides, such as glucose, fructose, and the like; disaccharides such as maltose, sucrose, oligosaccharides and the like; and polysaccharides for example, conventional sugars such as dextrin, cyclodextrin and the like, and sugar alcohols such as xylitol, sorbitol and erythritol. The flavoring agent may include natural flavoring agents such as thaumatin and stevia extract (for example, rebaudioside A and glycyrrhizin) and synthetic flavors (saccharin, aspartame, etc.).

As used herein, a term "administering" includes any method that allows a subject to have a therapeutic or preventive effect. For example, the administration includes dosing, injection, invasive topical infusion, intra-operative treatment, etc.

The route of administration of the pharmaceutical composition of the present invention may be determined as any conventional route so long as the composition can reach a target tissue along the route. The composition of the present invention may be administered intraperitoneally, intravenously, intramuscularly, subcutaneously, intradermally, orally, nasally, intrapulmonarily or intrarectally, or local injection, as desired. The present invention is not limited thereto. Further, the composition may be administered by any device by which the active substance may migrate to the target cell.

EXPERIMENTAL EXAMPLE

In order to facilitate understanding of the present invention, preferred Experimental Examples are presented below. However, the following Experimental Examples are provided only for the purpose of easier understanding of the present invention, and the present invention is not limited to the Experimental Example.

Materials

Preparation of Drug

Syringaresinol was purified from natural materials of Chemfaces (Wuhan, China) or synthesized by Hanchem (Daej eon, Korea). NBQX, picrotoxin, TTX, AP-5, DHPG, cyclothiazide and jasplakinolide were purchased from Tocris Cookson (Bristol, UK). All other reagents and chemicals were purchased from Sigma-Aldrich (MO, USA).

Preparation of Animals

All experiments were performed using male and female C57BL/6 mice of 4 to 6 weeks of age. An open field test was performed on male mice of 6 to 7 weeks. Animals were maintained with circulating 12/12-h day/night, while daytime starts at 07:00. Three or five animals were housed per one cage. Free available food and water were fed to the mice under specific pathogenic-microorganism free (SPF) conditions. The animal maintenance protocol and all experimental procedures were approved by the Institutional Animal Care and Use Committee (IACUC) of Seoul National University.

Preparation of Slice

A hippocampus slice (400 µm thick) was prepared in a cold dissection buffer using a vibrating machine (Vibratome, Leica, Germany) and then a CA3 region of each slice was removed surgically immediately after the slice formation. In this connection, the cold dissection buffer contained sucrose 230 mM; $NaHCO_3$ 25 mM; KCl 2.5 mM; $NaH_2PO_4$ 1.25 mM; D-glucose 10 mM; Na-ascorbic acid salt 1.3 mM; $MgCl_2$ 3 mM; $CaCl_2$ 0.5 mM, 95% $O_2$/5% $CO_2$ and had pH 7.4. The slice was recovered in a normal ACSF (artificial cerebrospinal fluid) for 1 hour and then maintained at room temperature (23 to 25° C.) until recording. In this connection, the normal ACSF (artificial cerebrospinal fluid) contained NaCl 125 mM; $NaHCO_3$ 25 mM; KCl 2.5 mM; $NaH_2PO_4$ 1.25 mM; D-glucose 10 mM; $MgCl_2$ 1.3 mM; $CaCl_2$ 2.5 mM, 95% $O_2$/5% $CO_2$ and had pH 7.4 and had a temperature 36° C.

Cell Culture and AMPA Receptor Expression

Human embryonic kidney cells (HEK293) were cultured in Dulbecco's modified Eagle's medium (DMEM) supplemented with 10% fetal bovine serum and 1% penicillin-streptomycin, and using a 5% $CO_2$ incubator as humidified at 37° C. The cells were grown in 12-well plates. EGFP (enhanced green fluorescent protein) was used alone according to the manufacturer's protocol using Lipofectamine 2000. EGFP was used as a selection marker for electrophysiological recording. The ratio of EGFP: GluAl or A3: GluA3 was 2:3:3 (total 2 µg per well). After 12 to 16 hours of incubation, the cells were washed twice with fresh, warm medium, all electrophysiological records were performed 48 to 72 hours after DNA cell infection.

Experimental Method

Electrophysiological Experiment

All electrophysiological experiments were performed in a recording chamber while the samples were immersed in the solution in a manner described previously (Song et al., 2017). Signals were amplified using a MultiClamp 700B amplifier (Molecular Devices, CA, USA) at a cut-off frequency of 2.8 kHz and were measured with a Digidata 1440A interface (Molecular Devices) at a 10 kHz sampling frequency. Data were collected using pClamp 10.2 (Molecular Devices) software. The collected data were analyzed with a program created in the lab using Igor Pro (WaveMetrics, OR, USA).

To record the field excitatory post-synaptic potential (fEPSP) in the hippocampal SC-CA1 synapse, hippocampal slices were placed in the recording chamber and perfused with ACSF while oxygen was fed continuously to the ACSF. The ACSF was maintained at a temperature of 29 to 30° C. using a heater for perfusion (SH-27B, Warner Instruments, CT, USA). A synapse response was induced by stimulation with a glass pipette (0.3 to 0.5 Mohm) every 20 seconds (0.05 Hz). The synapse response was recorded using a glass pipette (3 to 4 Mohm) filled with ACSF. The intensity of the stimulus was adjusted to produce a synapse response of about ⅓ of the maximum value thereof. The slices with unstable (10%) baseline records were excluded.

To measure evoked excitatory post-synaptic current (eEPSC), the synapse potential was recorded using a patch pipette (3 to 4Mohm) via the membrane voltage clamp technique. The patch pipette contained a solution containing 100 mM $CsMeSO_4$, 10 mM TEA-Cl, 20 mM CsCl, 8 mM NaCl, 10 mM HEPES, 0.5 mM QX-314-Cl, 4 mM Mg-ATP, 0.3 mM Na-GTP and 10 mM EGTA and having pH 7.25 and 290 mOsm/kg. EPSC was measured at a frequency of 0.05 Hz. The synaptic current was induced using a glass pipette (0.3 to 0.5 Mohm). $GABA_A$ receptor ($GABA_A$R) antagonist picrotoxin (50 μM) was added to ACSF. The stimulus intensity was adjusted to exhibit an EPSC peak amplitude of 100 to 250 pA at −70 mV. NMDA receptor-mediated EPSC (NMDAR-EPSC) was measured at −40 mV by adding picrotoxin and AMPA receptor blocker NBQX (10 μM) to ACSF.

An evoked inhibitory post-synaptic current (evoked IPSC, eIPSC) was measured at −70 mV using the same pipette solution as that used for eEPSC in the presence of NBQX (10 μM) and NMDAR blocker AP-5 (50 μM) in the ACSF. A stimulating electrode was placed on a radiating layer or a pyramidal cell layer near the target cell. IPSC was induced with paired-pulse stimulation (50 ms interval). The stimulus intensity was adjusted to exhibit a peak amplitude of 100 to 250 pA at a fixed potential of −70 mV. During eEPSC or eIPSC recording, series resistance and seal resistance were continuously observed using short hyperpolarization pulses (−5 mV, 50 ms). When the resistance was changed by more than 20% during recording, the data was discarded.

A miniature EPSC (mEPSC) was measured at −70 mV with a pipette solution. In this connection, the pipette solution contained 110 mM K-gluconate, 20 mM KCl, 8 mM NaCl, 10 mM HEPES, 0.5 mM QX-314-Cl, 4 mM Mg-ATP, 0.3 mM Na-GTP and 0.5 mM EGTA. The solution had pH 7.25 and 290 mOsm/kg. Voluntary action potentials and IPSCs were blocked by TTX (1 μM) and picrotoxin (50 μM), respectively. For mIPSC recording, the K-gluconate in the pipette solution was replaced with the KCl having the same number of moles as the K-gluconate. The current was measured at −70 mV in the presence of TTX (1 μM), NBQX (10 μM), and AP-5 (50 μM) in the ACSF.

To measure the membrane potential of neurons, whole-cell current clamp recordings were performed using the same pipette solution as that used for mEPSC recording, while excluding neurons that initially exhibited unstable resting membrane potentials.

The $Ca^{2+}$ channel current was measured using a pipette solution. The pipette solution contained 100 mM Cs-gluconate, 10 mM CsCl, 10 mM TEA-Cl, 8 mM NaCl, 10 mM HEPES, 4 mM Mg-ATP, 0.5 mM Na-GTP and 10 mM EGTA. The solution had a pH of 7.25 and 290 mOsm/kg. For $Ca^{2+}$ current measurements, TTX, NBQX, AP-5 and picrotoxin were added to ACSF, and $CaCl_2$ in ACSF was replaced by $BaCl_2$ with the same number of moles.

The current induced by glutamate in AMPAR-expressing HEK293 cells was measured at 30 mV using the same pipette solution as the solution used for recording the mEPSC except that a content of the EGTA was 10 mM. Glutamate (10 μM) was applied using a bath solution (adjusted to pH 7.4 with NaOH). The bath solution contained 140 mM NaCl, 5 mM KCl, 1.25 mM $NaH_2PO_4$, 2 mM $CaCl_2$, 1 mM $MgCl_2$, 10 mM D-glucose, and 10 mM HEPES and was heated to 29 to 30° C. Cyclothiazide (100 μM) was added to the perfusion solution to inhibit desensitization of AMPAR.

Western Blotting

After removing the CA3 region from the hippocampal slice surgically, the slices were recovered in the 36° C. and normal ACSF for 4 hours. Each sample was treated with each drug for 10 minutes, and then frozen using liquefied nitrogen. Western blot analysis of drug-induced changes in ERK activity in the hippocampal slices was performed in a manner as previously described (Song et al., 2017). The slices were homogenized using a probe sonicator in a cold lysis buffer about at a temperature of ice. The lysis buffer contained 50 mM HEPES, 100 mM NaCl, 5 mM EGTA, 5 mM EDTA, 1% Triton X-100, a phosphatase inhibitor mixer (GenDEPOT, TX, USA) and a protease inhibitor mixer (Sigma-Aldrich, MO, USA). The total protein concentration of the homogenate was determined by Bradford protein assay (Bio-Rad, CA, USA). Samples containing 10 to 12 μg of protein were separated using SDS-PAGE gels and transferred to the nitrocellulose membrane. The membrane was sequentially reacted with a primary antibody (p-ERK and ERK; Cell Signaling Technologies, MA, USA) and a secondary antibody (Jackson ImmunoResearch, USA) having horse radish peroxidase (HRP) coupled thereto. HRP signals were detected on an enhanced chemiluminescence (ECL) substrate (GE Healthcare, UK) and then quantified with MetaMorph software (Molecular Devices, CA, USA).

Statistical Analysis

All results were expressed as mean±SEM. Statistical analysis was performed using Igor Pro (WaveMetrics, OR, USA) and SPSS (IBM, NY, USA). Statistical significance was determined by Student's t-test. When the number of groups to be analyzed is large, statistical significance was measured using one-way ANOVA with a post hoc Tukey's HSD test.

Experimental Example 1

Effect of Syringaresinol on SC-CA1 Synapse

Figure 1B:
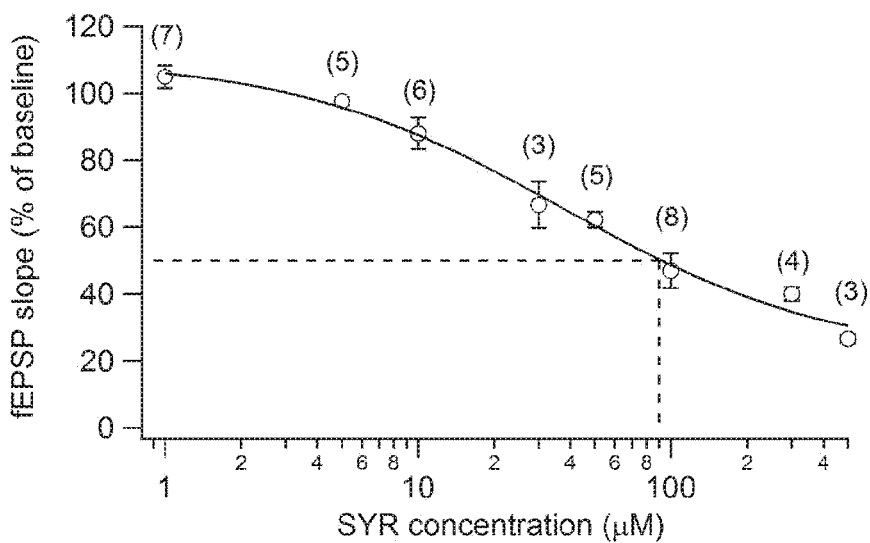
FIG. 1B shows a dose-response curve for the SYR-induced-inhibition of the fEPSP slope.
Figure 1C:
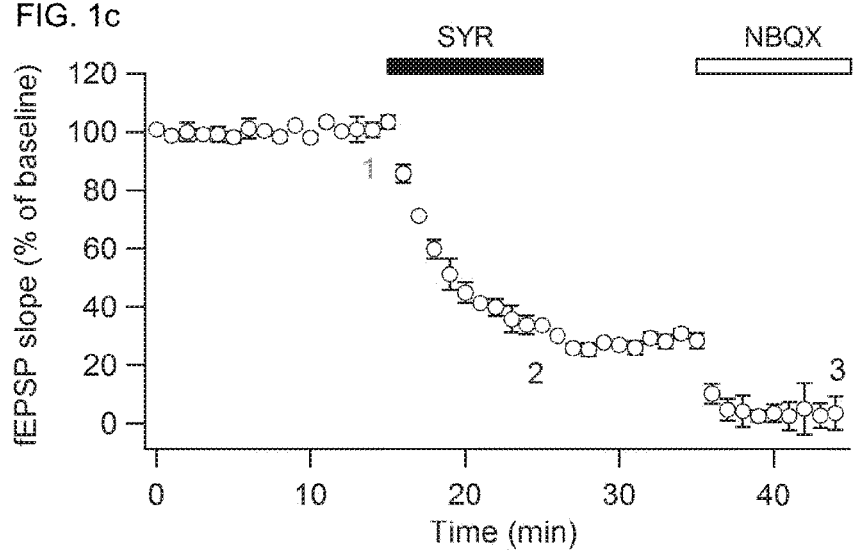
FIG. 1C shows that excitatory synaptic transmission is reduced by SYR and completely blocked by NBQX.
Figure 1D:
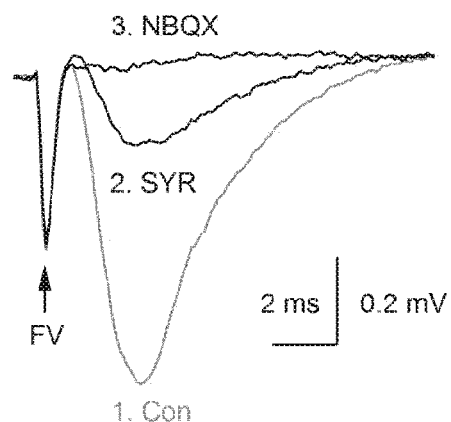
FIG. 1D shows a sample trace of the fEPSP recorded during a baseline (1. Con, 14 to 15 min), SYR perfusion (2. SYR, 24 to 25 min), and NBQX perfusion (3. NBQX, 44 to 45 min) in FIG. 1C.
Figure 1E:
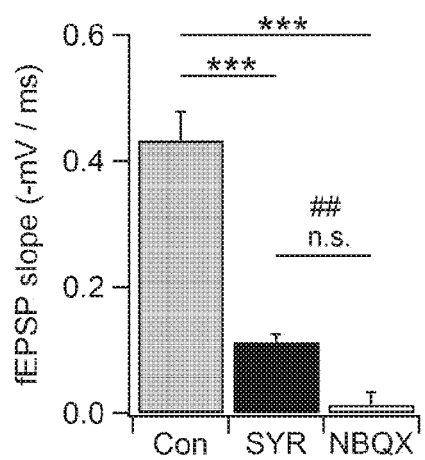
FIG. 1E is a histogram showing a slope of the average fEPSP over each of the baseline and the last two minutes of drug application (n=3 hippocampal slices; ***$p<0.001$; n.s., not significant ($p>0.05$); $F_{(2,6)}=2.93$; one-way ANOVA with a Bonferroni post hoc test; ## $p<0.01$; $t=4.64$; Student's t-test).

To investigate the effect of syringaresinol (SYR) on the synaptic transmission, the field excitatory post-synaptic potential (fEPSP) of the Schaffer collateral (SC)-CA1 synapse of the hippocampus of adult mice (4 to 6 weeks of age) was measured. After confirming the stable baseline, different concentrations of SYR were applied thereto using the perfusion solution. Low concentrations of SYR (1 to 5 μM) did not affect fEPSP. At high concentrations (>10 μM) of SYR, the post-synaptic response decreased rapidly (FIG. 1A). As the concentration of SYR increased, the slope and amplitude of fEPSP decreased in a concentration-dependent manner (IC50=90 μM). Further, the maximum inhibition (75.9±1.6%) was exhibited at 500 μM of SYR (FIG. 1B). A pre-synaptic fiber volley was not affected by SYR. This suggests that the number of stimulated axons did not change. A portion reduced by SYR during the synaptic response was completely blocked by the AMPA receptor blocker NBQX (10 μM) (FIG. 1C to FIG. 1E). These results indicate that SYR inhibits excitatory transmission in SC-CA1 synapse.

Figure 1F:
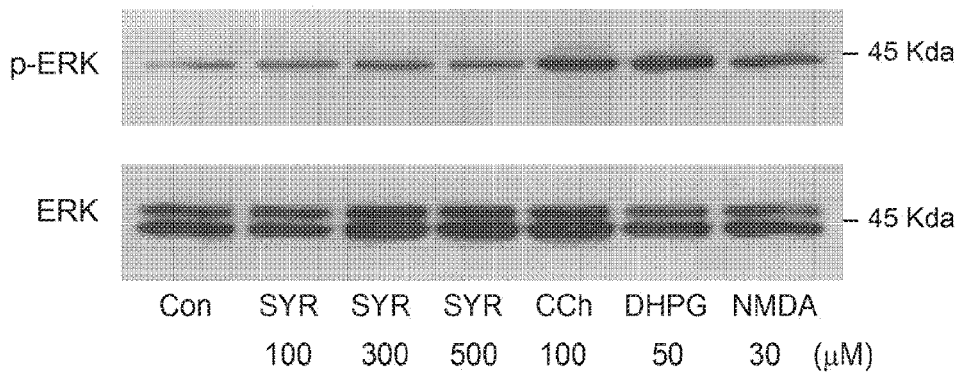
FIG. 1F shows a typical western blot of p-ERK and ERK at each treatment condition.
Figure 1G:
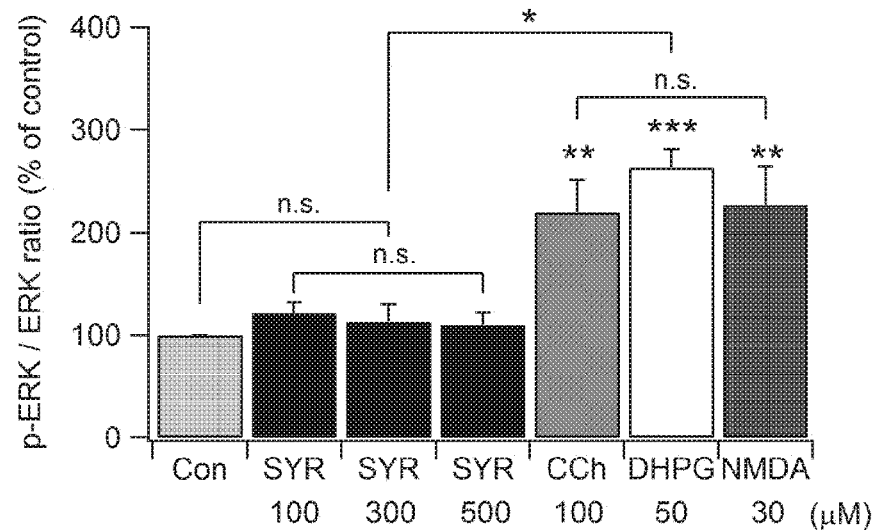
FIG. 1G shows, at a percentage, a degree of activation of ERK in each condition compared to a control (Con) (n=7 independent blots, n.s., not significant ($p>0.05$); *$p<0.05$; $p<0.01$; *$p<0.001$; $F_{(6,42)}=1.29$; one-way ANOVA with a Bonferroni post hoc test).

The activity of the NMDA receptor (NMDAR), the group I metabotropic glutamate receptor (mGluR), or the metabolic acetylcholine receptor (mAChR) is known to inhibit AMPAR-mediated synaptic transmission in SC-CA1 synapse for a long period of time. The activity of ERK is related to a sub-signaling pathway of synapse inhibition mediated by these receptors. In order to determine whether SYR-induced synapse inhibition is associated with the activity of these receptors, the effect of high concentrations (100, 300 and 500 μM) of SYR on ERK activity (FIGS. 1F and 1G) were examined. Unlike the mAChR agonist carbachol (CCh), the group I mGluR antagonist DHPG and NMDAR agonist NMDA, the SYR did not affect ERK activity ($F_{(6, 42)}=1.29$, $p>0.05$, one-way ANOVA with a Bonferroni post hoc test, FIG. 1G). This finding suggests that SYR induces synaptic inhibition using a pathway distinct from the general mechanism of the post-synaptic suppression.

Experimental Example 2

Effect of SYR on Inhibitory Synaptic Transmission

Figure 2A:
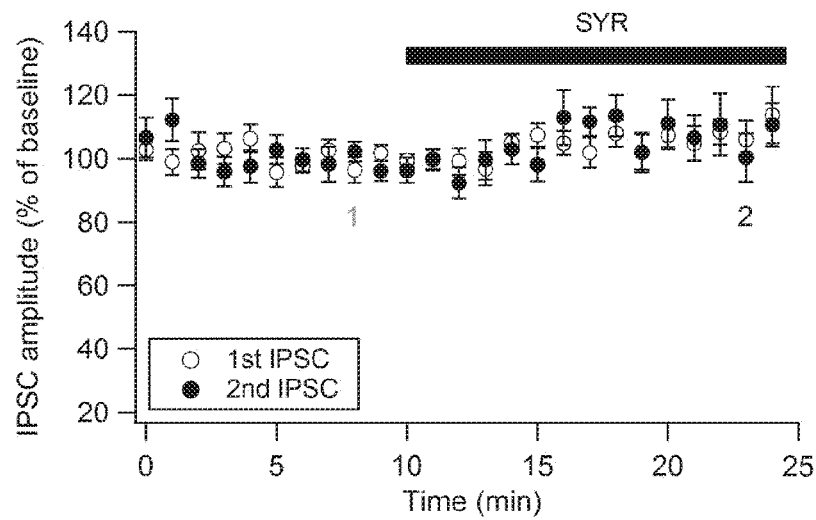
FIG. 2A shows a peak amplitude of IPSC induced by paired-pulse (100 ms interval) stimulation.
Figure 2B:
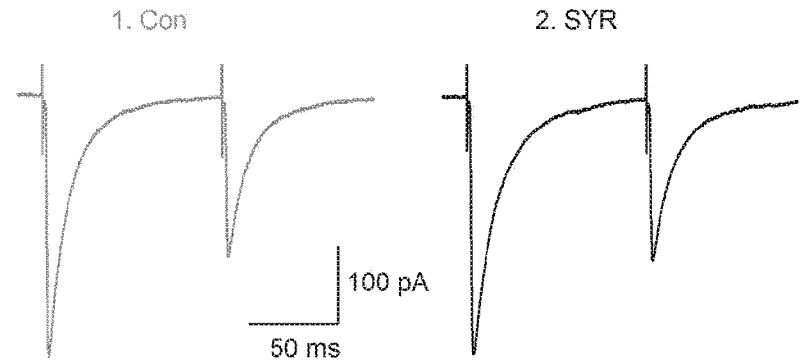
FIG. 2B shows the IPSC (average of 6 consecutive reactions) recorded at the time indicated on the graph in FIG. 2A (1, 2).
Figure 2C:
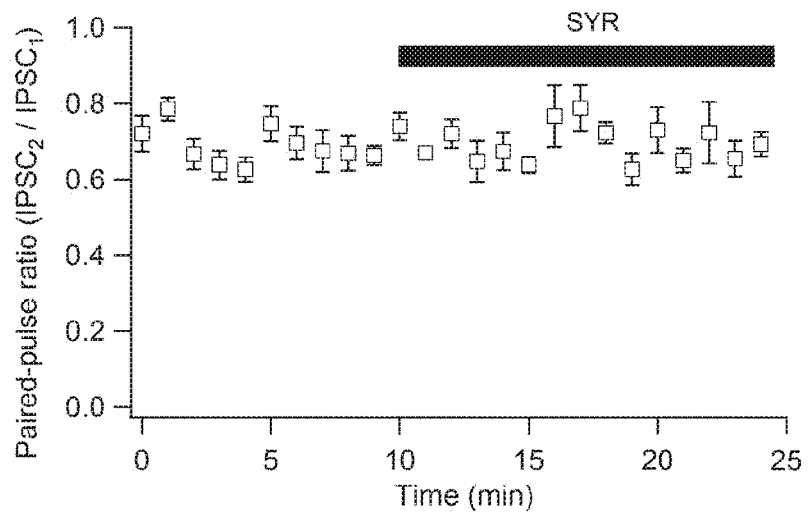
FIG. 2C shows, over time, a paired-pulse ratio (PPR) of the IPSC induced by the stimulus applied to Panel A.
Figure 2D:
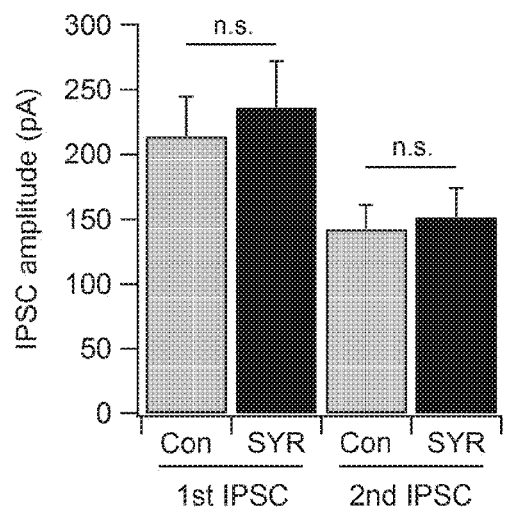
FIG. 2D and FIG. 2E show that the SYR does not affect the first or second IPSC (D), and PPR (E), where bar graphs show respectively averages of the IPSC amplitude and PPR for the baseline and the last two minutes of SYR application.
Figure 2E:
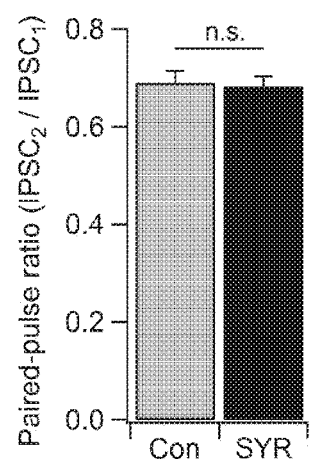

SYR inhibits inhibitory synaptic transmission in CA1 neurons. Thus, the effect of the SYR on the inhibitory synaptic transmission was checked by measuring the inhibitory post-synaptic current (IPSC) in the presence of the AMPAR blocker NBQX and the NMDAR blocker AP-5 (FIG. 2A). IPSC (eIPSC) induced by a pair of stimuli at 100 ms intervals showed paired-pulse inhibition in CA1 neurons (FIG. 2B and FIG. 2C). In contrast to the effect of the SYR on the excitatory transmission, SYR (100 μM) had no effect on eIPSC (FIG. 2A). There was no difference between the first eIPSC (t=−0.47, $p>0.05$) and the second eIPSC (t=−0.33, $p>0.05$) as measured before and after the application of SYR respectively. The ratio (t=0.23, $p>0.05$) of the ISPC amplitude induced by paired-pulse stimulation did not change (FIGS. 2D and 2E). These results indicate that SYR does not affect $GABA_AR$ or pre-synaptic GABA release.

Figure 2F:
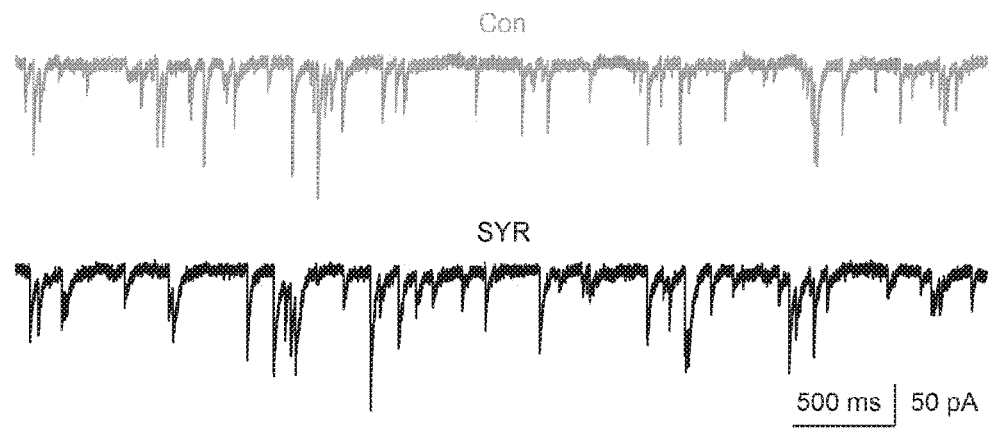
FIG. 2F shows the mIPSC recorded in CA1 neurons under the absence (Con) and presence of SYR.
Figure 2G:
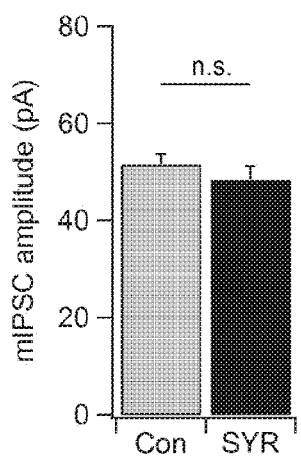
FIG. 2G and FIG. 2H show respectively the mean amplitudes (G) and frequencies (H) of mIPSC before and after SYR application (n=9 cells, n.s., not significant ($p>0.05$), Student's t-test (D, E, G, H)).
Figure 2H:
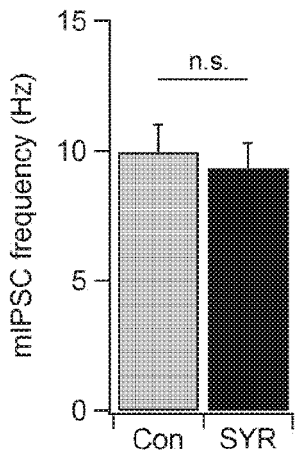

The effect of SYR on the miniature IPSC (mIPSC) was checked. As shown in FIG. 2F, the application of SYR did not make any appreciable changes in the mIPSC. When quantifying this result, we found that SYR did not affect the amplitude of mIPSC (t=1.0, $p>0.05$) or frequency (t=1.04, $p>0.05$) thereof (FIG. 2G and FIG. 2H). This means that SYR does not affect both eIPSC and mIPSC.

Experimental Example 3

Effect of SYR on AMPAR Function

Figure 3A:
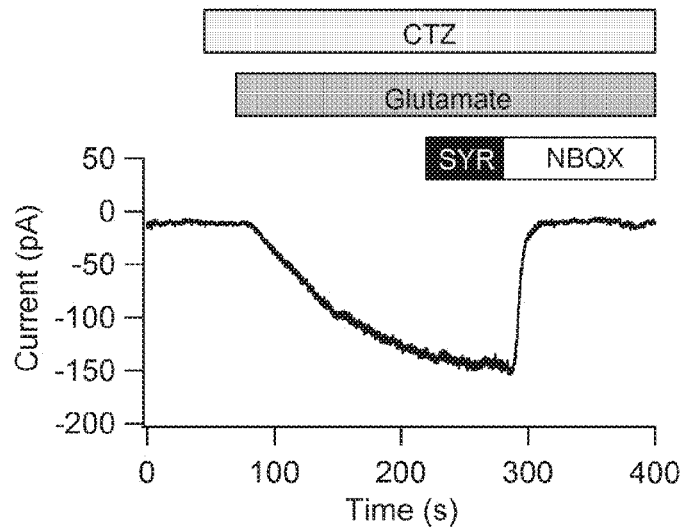
FIG. 3A shows the effect of SYR and NBQX on glutamate-induced currents in GluA1/2-expressing HEK293 cells.
Figure 3B:
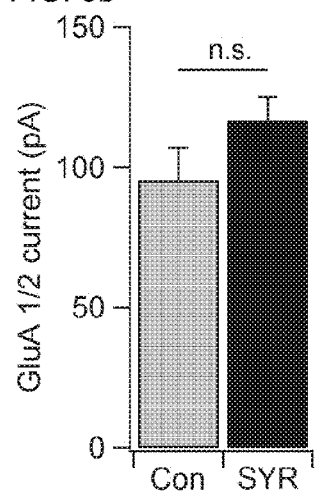
FIG. 3B shows respectively mean amplitudes of glutamate-induced currents in GluA1/2-expressing HEK293 cells before and after SYR perfusion (n=4 cells, $t=2.12$, $p>0.05$, Student's t-test).
Figure 3C:
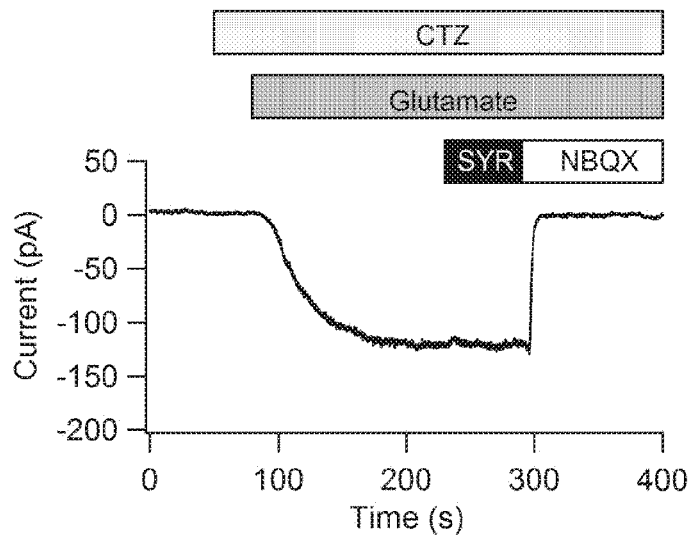
FIG. 3C shows a representative trace of a glutamate-induced current in HEK293 cells expressing subunit GluA2/3 of AMPAR.
Figure 3D:
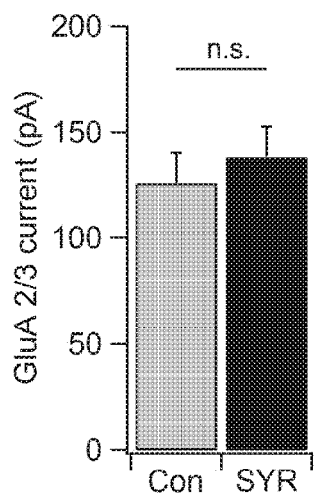
FIG. 3D shows the effect of SYR and NBQX on the current induced by glutamate in GluA2/3-expressing HEK293 cells (n=5 cells, $t=0.61$, $p>0.05$, Student's t-test).

The effect of SYR on the glutamate-induced current of HEK293T cells expressing AMPAR was checked. Since the AMPAR of CA1 neurons is a heteromer composed mainly of GluA1/2 or GluA2/3 subunits, GluA2 was expressed together with GluA1 or GluA3 in HEK293T cells. In the presence of cyclothiazide (CTZ, 100 μM) as an AMPAR desensitization blocker, the application of glutamate (10 μM) produced a long-sustained current in HEK293T cells (FIG. 3A and FIG. 3C). This current was not affected by SYR but was rapidly blocked by the AMPAR blocker NBQX in both GluA1/2 and GluA2/3-expressing cells (FIG. 3A to FIG. 3D). These results show that AMPAR mediates the glutamate-induced current in cells and that SYR does not directly inhibit AMPAR.

Figure 3E:
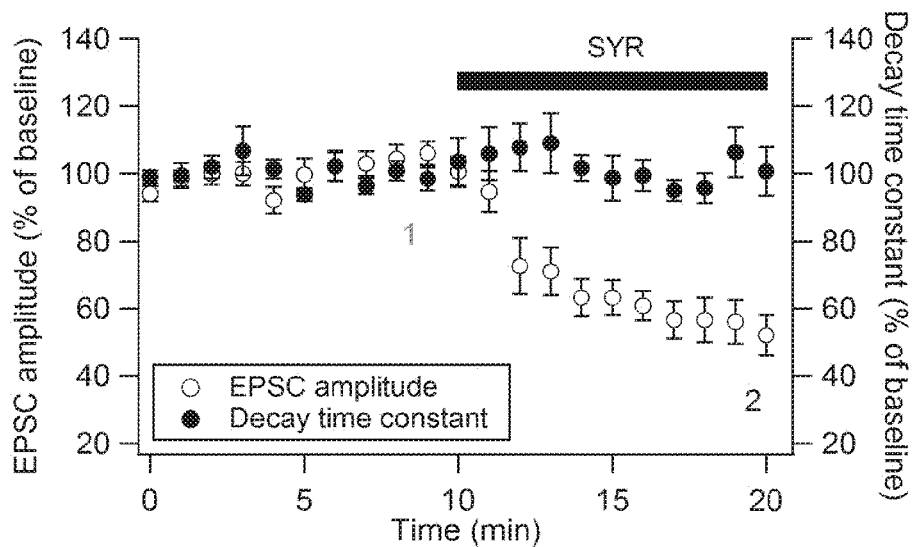
FIG. 3E shows that the application of SYR reduces the amplitude of EPSC measured at a fixed potential of 70 mV in CA1 neurons.
Figure 3F:
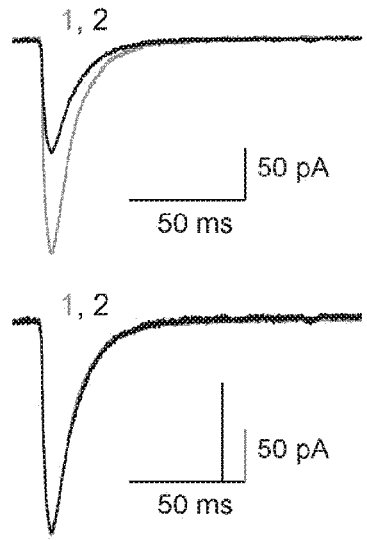
FIG. 3F (an upper drawing) shows EPSC (average of 6 consecutive sweeps) measured at the time indicated in FIG. 3E (1, 2).
Figure 3G:
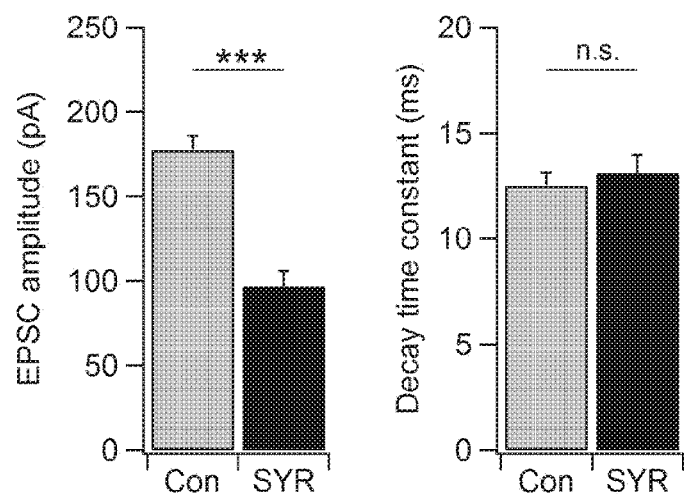
FIG. 3G shows that SYR reduces the EPSC amplitude ($t=6.62$, $p<0.001$) without affecting the decay time constant of EPSC ($t=0.56$, $p>0.05$) (n=9 cells, Student's t-test).

If SYR modulates the desensitization of AMPAR, the effect of SYR will not be observed in the above experimental conditions due to the presence of CTZ. Thus, it was necessary to check the effect of SYR on desensitization of AMPAR in CA1 neurons. The whole-cell patch clamp technique was used in the presence of NMDAR blocker AP-5 and $GABA_A$ receptor blocker picrotoxin (PTX, 50 μM). In a similar manner to the fEPSP result, SYR significantly reduced the excitatory post-synaptic current (EPSC) at a fixed potential of −70 mV (FIG. 3E). However, the descending phase of AMPAR-mediated EPSC (AMPAR-EPSC) was not affected by SYR. The normalized EPSC measured in the presence of SYR overlapped well with the control result (FIG. 3F; upper and lower drawings). Therefore, SYR did not affect the time constant of EPSC reduction (FIG. 3G). The possibility that SYR could reduce excitatory synaptic transmission through AMPAR desensitization was ruled out.

Figure 3H:
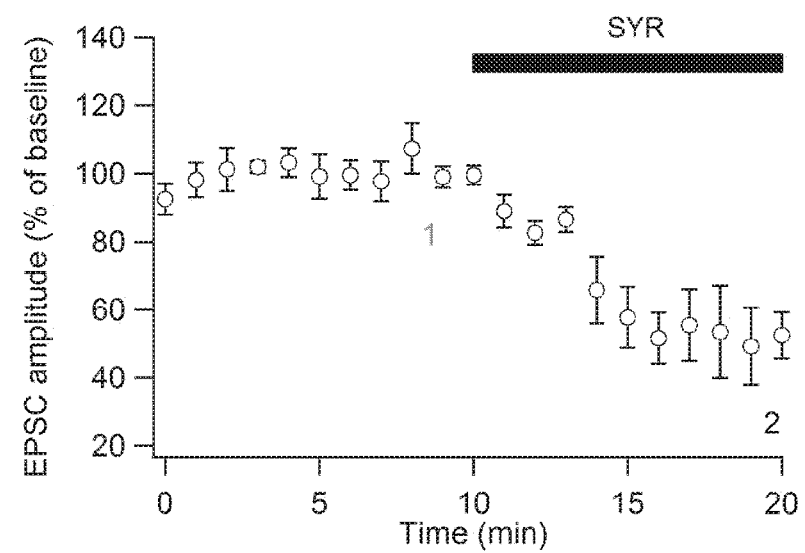
FIG. 3H shows, as a percentage relative to that of the baseline, a peak amplitude of EPSC as measured with a pipette solution containing jasplakinolide (2 microM).
Figure 3I:
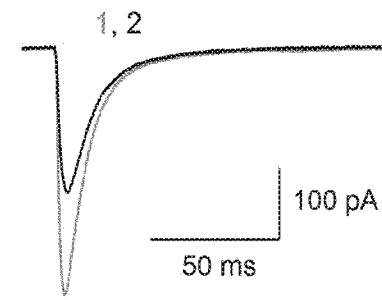
FIG. 3I show sample traces of EPSC as measured during the baseline (1) and SYR perfusion (2) of FIG. 3H.
Figure 3J:
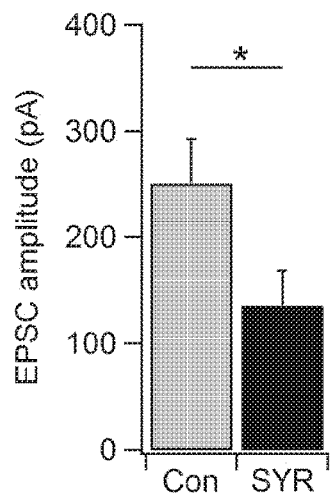
FIG. 3J shows that jasplakinolide as an actin-stabilizing agent does not affect the synapse transmission inhibition by SYR (n=4 cells, $t=4.41$, $p<0.05$, Student's t-test).

Although SYR did not directly regulate AMPAR, the AMPAR-mediated fEPSP and AMPAR-EPSC of CA1 synapse were reduced by SYR. In particular, SYR did not affect inhibitory synapse transmission. Because inhibitors of actin polymerization affect excitatory synaptic transmission (Xia et al., 2016), it is assumed that the discrepancy between normal AMPAR function and reduced AMPAR-mediated synaptic transmission may be due to actin-dependent structural modification of dendrites in neurons. To confirm this assumption, we examined the effect of SYR on AMPAR-EPSC by injecting, as the actin-stabilizer, jasplakinolide (2 μM) into the patch pipette solution (FIG. 3H to FIG. 3J). As a result, it was confirmed that SYR-induced inhibition was not related to actin depolymerization.

Figure 3K:
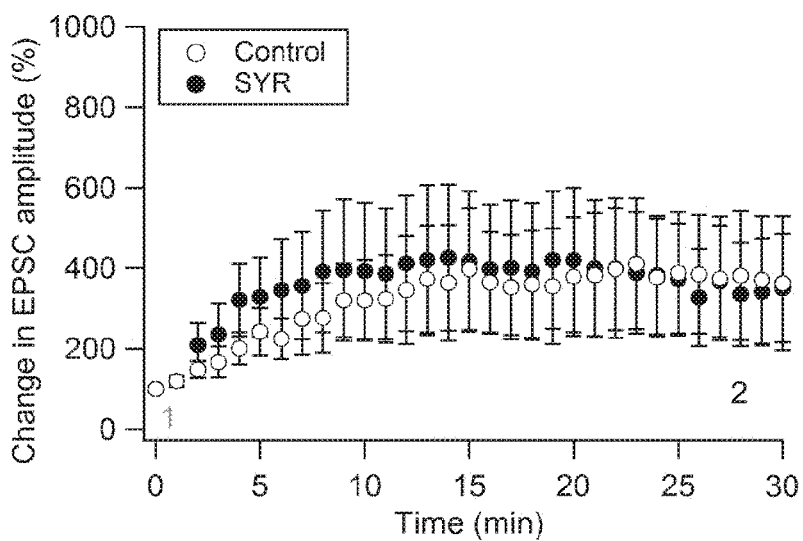
FIG. 3K shows a relative change in a peak amplitude of EPSC measured in the absence and presence of SYR in the pipette solution as a result of showing that SYR acts outside the cell.
Figure 3L:
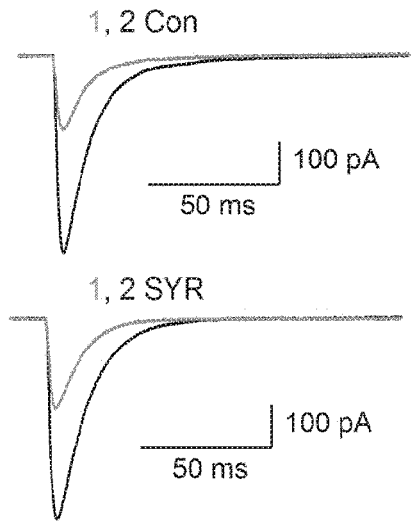
FIG. 3L shows a sample trace (upper drawing: control; a lower drawing: SYR) of the EPSC recorded at the time indicated in the graph of FIG. 3K (1, 2).
Figure 3M:
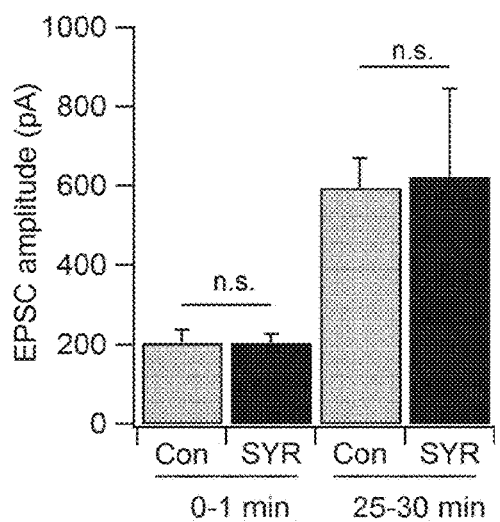
FIG. 3M summarizes the EPSC mean amplitude ($t=0.14$, $p>0.05$ at 0 to 1 min; $t=0.13$, $p>0.05$ at 25 to 30 mins; n=5 (Con) and =4 (SYR) cells; Student's t-test).

Furthermore, we checked whether post-synaptic loading of SYR regulates AMPAR-EPSC. We measured AMPAR-EPSC for 25 minutes immediately after cell membrane-punching using a K+-based pipette solution. In the absence of SYR in the pipette solution, AMPAR-EPSC gradually increased and remained stable (FIG. 3K). If the post-synaptic loading of SYR affects AMPAR-EPSC, gradual diffusion of SYR from the pipette solution should inhibit AMPAR-EPSC. However, actually, the magnitude and time lapse of the relative change in the AMPAR-EPSC amplitude were not affected by the gradual intracellular spread of SYR (FIG. 3K to FIG. 3M).

Experimental Example 4

Effect of SYR on Pre-Synaptic Function in SC-CA1 Synapse

Figure 4A:
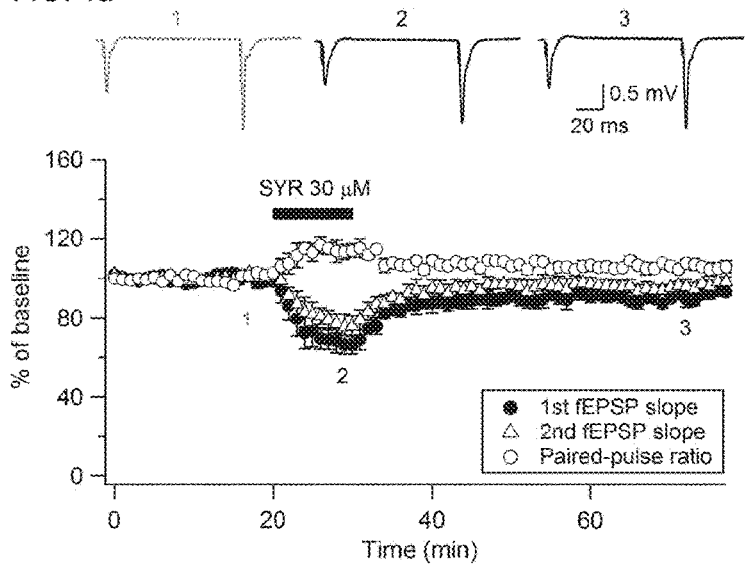
FIG. 4 shows that the SYR affects the PPR of the excitatory synaptic transmission. More specifically, FIG. 4A (30 microM) and 4B (100 microM) show that the SYR increases the PPR of fEPSP, where fEPSP is shown as a percentage relative to that of the baseline. The sample traces of the fEPSP were measured before (1), during (2) and after (3) the bath application of SYR.
FIG. 4C shows the statistical analysis of the experiment shown in FIG. 4A. This indicates that the 30 μM SYR decreases a first fEPSP slope ($t=11.0$, $p<0.01$) and a second fEPSP slope ($t=10.6$, $p<0.01$) and increases PPR ($t=2.58$, $p<0.05$) (N=4 slices, Student's t-test).
FIG. 4D shows a summary of the experiment in FIG. 4B (first fEPSP: $t=12.1$, $p<0.001$; second fEPSP: $t=7.5$, $p<0.01$; PPR: $t=3.03$, $p<0.05$; n=5 slices, Student's t-test).
FIG. 4E shows the slope of the fEPSP recorded before and during the 1-hour SYR application, for the time as normalized with a percentage relative to that of the baseline.
FIG. 4F shows sample traces of fEPSP induced by paired-pulse stimulation at various intervals.
FIG. 4G shows the recorded PPR over the inter-stimulus interval under the absence or presence of SYR ($t=12.5$ (20 ms), $t=5.67$ (50 ms), $t=5.11$ (100 ms), $t=3.63$ (200 ms), *$p<0.001$, $p<0.01$, n=14 slices, Student's t-test).
FIG. 4H shows the first NMDAR-EPSC peak amplitude induced by paired-pulse (100 ms interval) stimulation.
FIG. 4I shows representative traces of NMDAR-EPSC recorded before and after the SYR perfusion.
FIG. 4J summarizes the mean charge shifts measured over the baseline and the last two minutes of SYR application ($t=7.64$, $p<0.001$, n=11, Student's t-test).
Figure 4B:
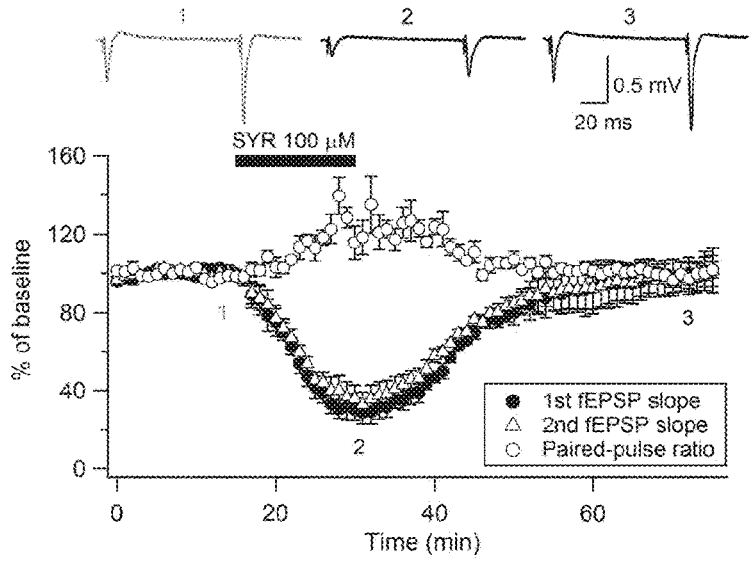
Figure 4C:
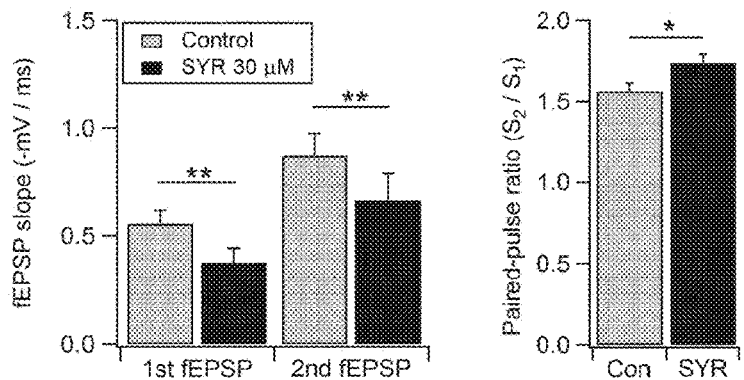
Figure 4D:
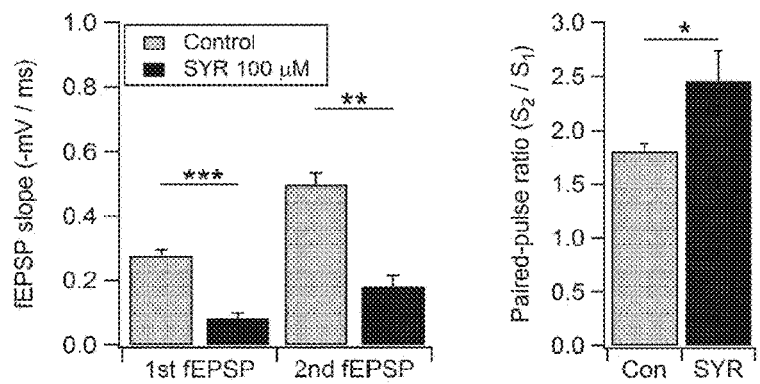

We checked whether SYR regulates excitatory pre-synaptic function. The paired-pulse ratio (PPR) of fEPSP was observed over the entire recording duration (FIG. 4A to FIG. 4D). Both the first and second fEPSPs (interval 100 ms) were significantly decreased by low concentration (30 μM) SYR and high concentration (100 μM) SYR. However, the PPR gradually increased as the slope of fEPSP decreased. This means that SYR reduces the secretion of neurotransmitters from the pre-synaptic terminals. After washing the SYR with control solution, PPR and fEPSP slowly recovered to baseline (FIG. 4A and FIG. 4B). These results indicate that SYR causes transient inhibition of excitatory synaptic transmission.

Figure 4E:
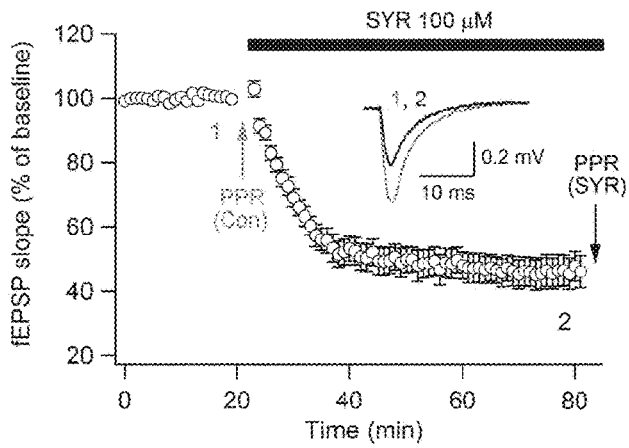
Figure 4F:
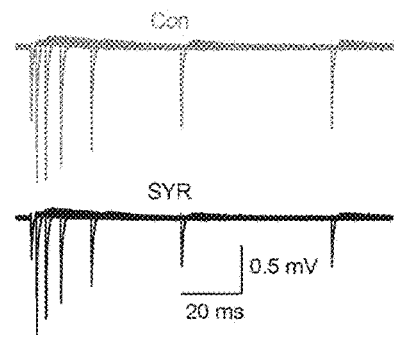
Figure 4G:
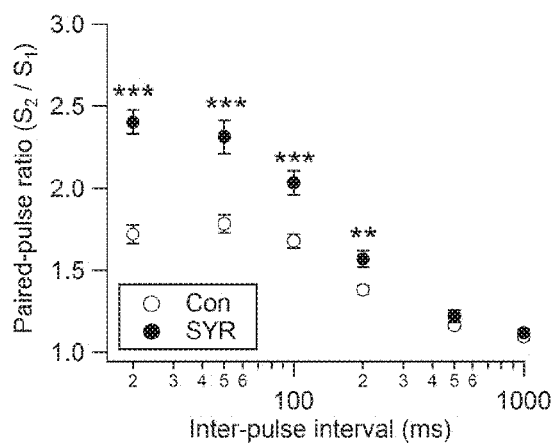

Next, we analyzed the effect of SYR on the PPR of the interval between various pulses. During SYR perfusion (1 h) at a concentration of 100 μM, the amplitude of fEPSP rapidly decreased and then remained stable throughout the entire recording duration (FIG. 4E). When comparing PPRs measured before the application of SYR and measured one hour after the application of SYR, there was no difference in PPR when the inter-pulse interval was large 500 ms). However, there was a significant difference in PPR when the inter-pulse interval is small 200 ms) (FIG. 4F and FIG. 4G).

Figure 4H:
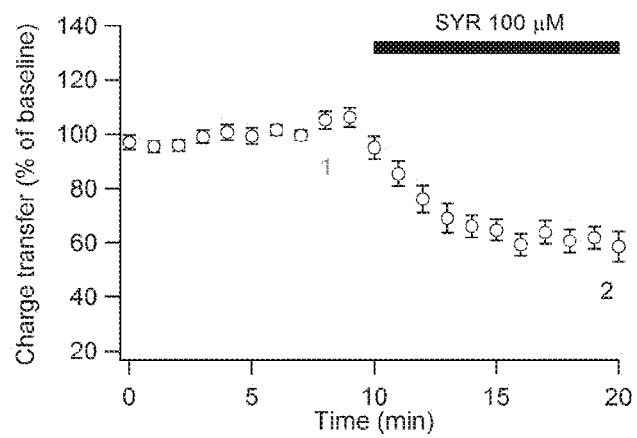
Figure 4I:
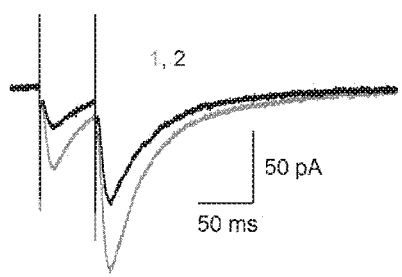
Figure 4J:
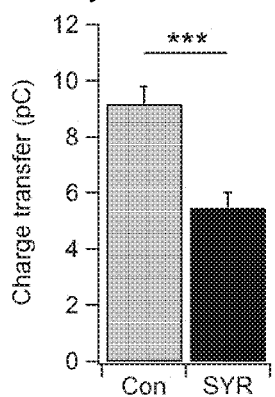

If SYR reduces pre-synaptic glutamate release, the effect of SYR should be observed in NMDAR-mediated EPSC (NMDAR-EPSC). NMDAR-EPSC was measured at −40 mV in the presence of NBQX and picrotoxin. In fact, SYR significantly inhibited NMDAR-EPSC induced by paired-pulse stimulation having 100-ms interval (FIG. 4H to FIG. 4J). When considering that SYR inhibits AMPAR-EPSC and NMDAR-EPSC, respectively, in the presence of AP-5 and NBQX and thus the excitatory PPR at a short interval is changed by SYR, it is valid that SYR affects pre-synaptic glutamate release.

Experimental Example 5

Checking of Regulation of Synaptic Vesicle Pool Size in SC-CA1 Synapse by SYR

Figure 5A:
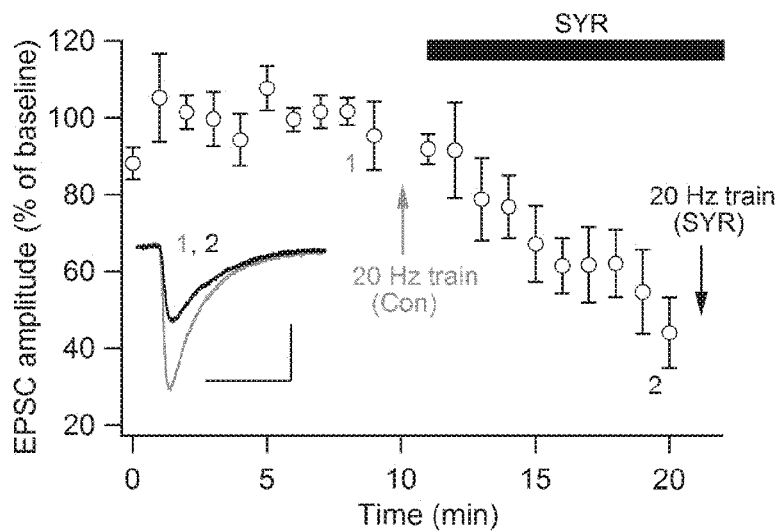
FIG. 5A shows, over time, the mean amplitude of EPSC measured before and during SYR perfusion as a percentage relative to that of the baseline.
Figure 5B:
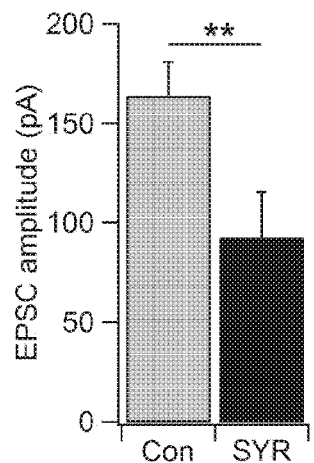
FIG. 5B shows a mean amplitude of EPSC measured over the baseline and the last two minutes of SYR perfusion as the result shown in FIG. 5A.
Figure 5C:
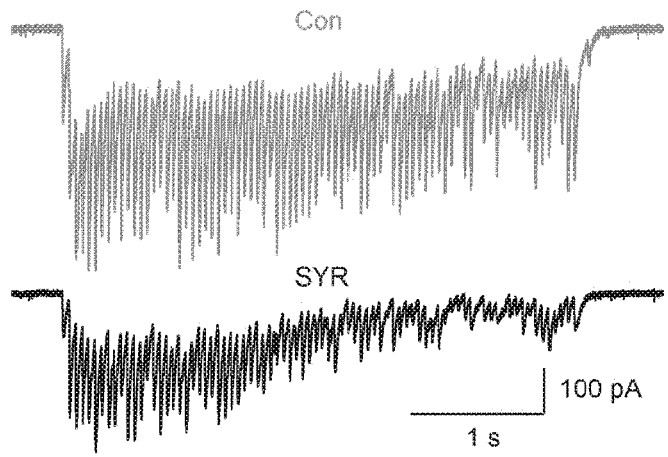
FIG. 5C shows representative traces of EPSC induced by high-frequency (20 Hz) stimulation under the absence (Con) and presence (SYR) of SYR.
Figure 5D:
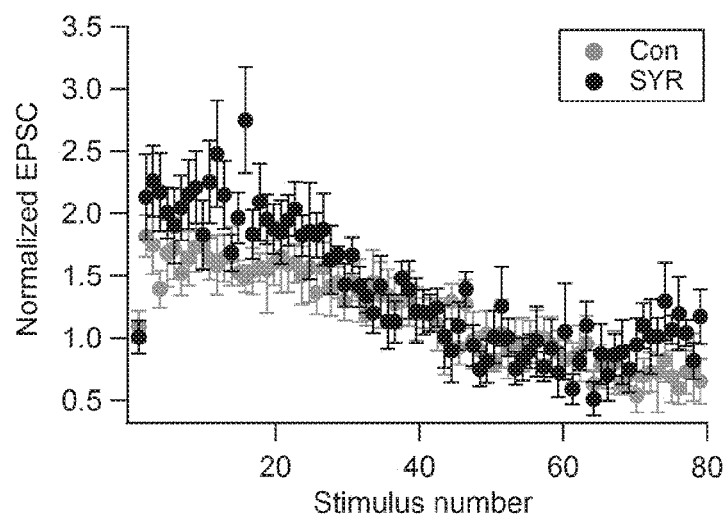
FIG. 5D shows EPSC as induced by 80 stimuli at 20 Hz under the absence and presence of SYR as the number of stimuli as normalized with the first peak.
Figure 5E:
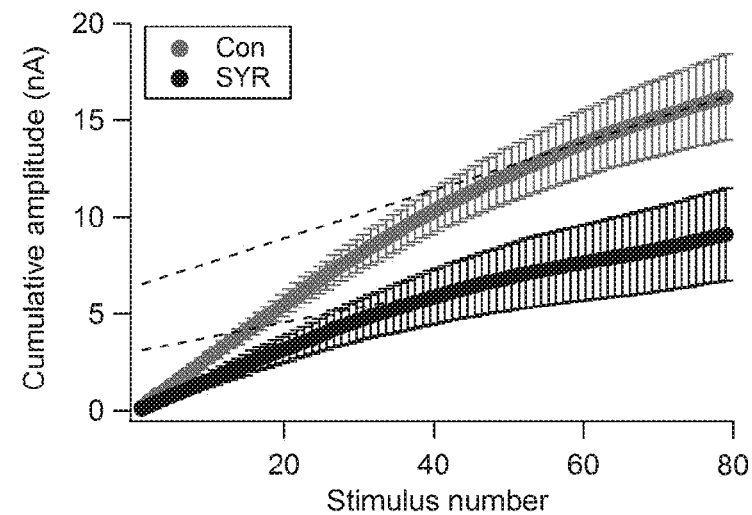
FIG. 5E shows the amplitude of EPSC with respect to the number of stimuli.
Figure 5F:
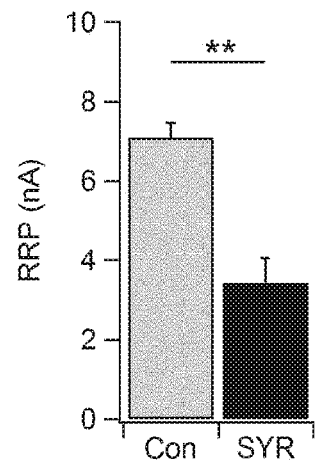
FIG. 5F shows the linear regression of the RRP size during synapse recruitment ($t=4.84$, $p<0.01$, n=6 cells, Student's t-test).
Figure 5G:
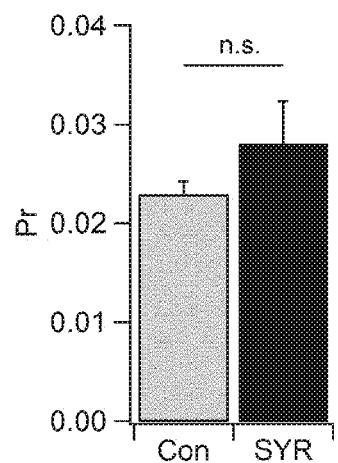
FIG. 5G shows the average emission probability (Pr) by dividing the size (F) of the synaptic vesicle with the average amplitude (B) of the EPSC under each condition.

Previous studies have shown that the secretion probability is regulated by the size of the readily releasable pool (RRP) of hippocampal neurons. Therefore, RRP was measured before and after treatment with SYR (100 μM). A high-frequency train (20 Hz) composed of more than 60 stimuli was prepared. 80 stimuli at 20 Hz was applied to completely remove RRP from the SC-CA1 synapse. RRP size was measured by cumulative amplitude analysis (Stevens and Williams, 2007; Wesseling and Lo, 2002). In the presence of AP-5 and picrotoxin, SYR inhibited AMPAR-EPSC (FIG. 5A and FIG. 5B). Furthermore, from the results of linear regression analysis from the last 20 points of cumulative EPSC amplitude (3 to 4s in the stimulus train), it was confirmed that SYR application resulted in a significant decrease in the RRP size (FIG. 5C to FIG. 5F). An extent by which RRP size is reduced was very close to an extent by which synapse is inhibited (FIG. 5B and FIG. 5F). However, the secretion probability (Pr) of individual synaptic vesicle measured from the average of EPSC amplitude and RRP size was not changed by SYR (FIG. 5G). This means that a decrease in RRP size may lead to the SYR-induced synapse decrease.

Figure 5H:
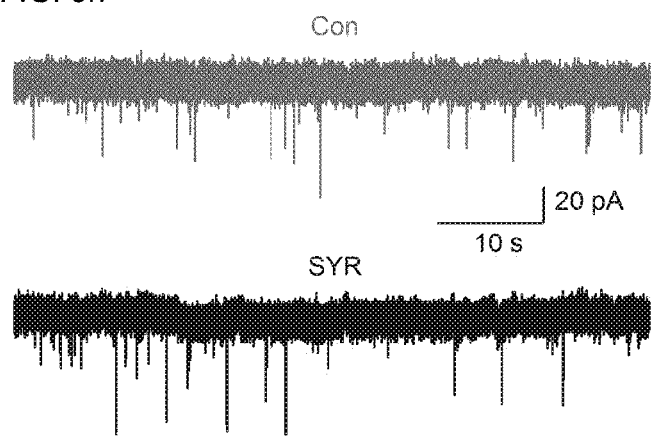
FIG. 5H shows sample traces of mEPSC as recorded before and after SYR application.
Figure 5I:
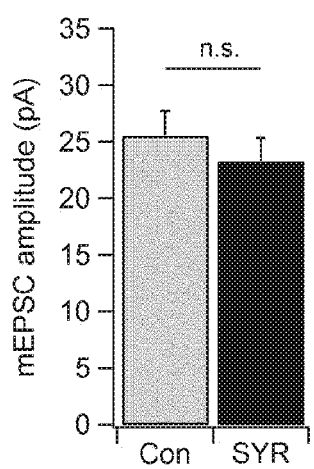
FIG. 5I and FIG. 5J show that SYR does not affect the amplitude of mEPSC ($t=0.87$, $p>0.05$; I) or frequency thereof ($t=0.80$, $p>0.05$; J) (n=13 cells, Student's t-test).
Figure 5J:
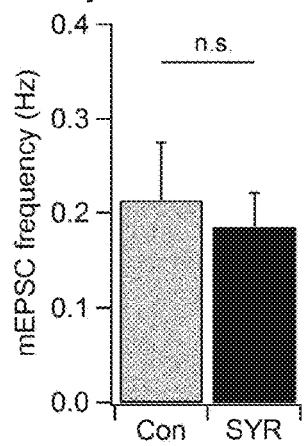

Next, the effect of SYR on miniature EPSC (mEPSC) in CA1 neurons was examined. In contrast to eEPSC, mEPSC did not change in frequency and amplitude (FIG. 5H to FIG. 5J). Considering that mEPSC and eEPSC are mediated by different synaptic vesicle pools (Sara et al., 2005), the unchanged mPESC indicates that SYR regulates mainly an active-dependent synaptic vesicle pool.

Experimental Example 6

Effect of SYR on Neural Cell Resting Membrane Potential

Figure 6A:
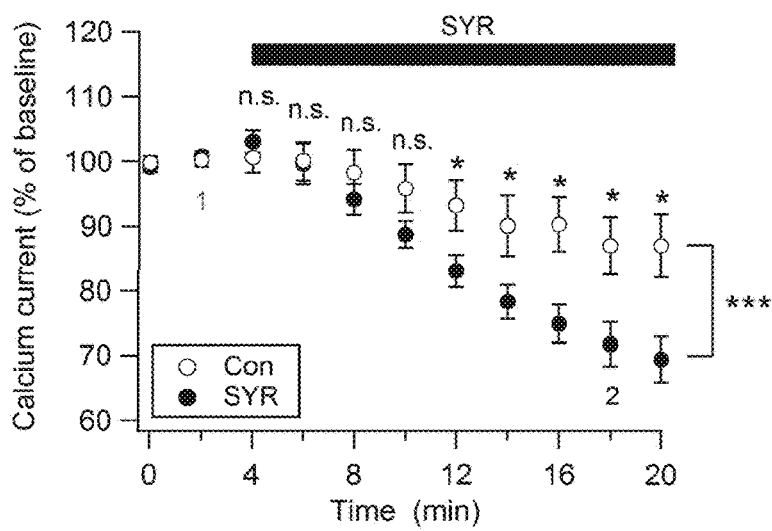
FIG. 6A shows the peak amplitude of $Ca^{2+}$-channel current over time in control and SYR perfusion [n=6 (Con) and 7 (SYR) cells, *$p<0.05$ by Student's t-test; ***$p<0.001$, $F_{(1,16)}=28.84$ by two-way ANOVA with a post hoc Tukey's HSD test].
Figure 6B:
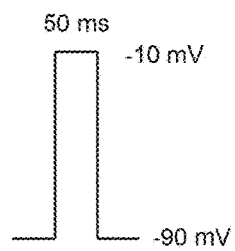
FIG. 6B shows the membrane voltage protocol for $Ca^{2+}$ channel current recording.
Figure 6C:
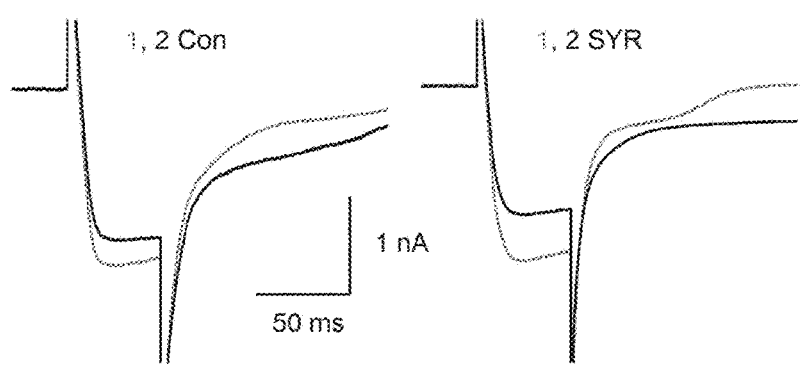
FIG. 6C shows the sample trace (left) of the $Ca^{2+}$ channel currents measured at 2 min (gray) and 18 min (black) during recording for a control ACSF and the sample trace (right) of the Ca²⁺ channel currents measured before (2 min) and after (18 min) the application of SYR.

Reduced $Ca^{2+}$ influx to the pre-synaptic terminal leads to synapse degradation in central synapse. To explore this possibility, we analyzed the effect of SYR on $Ca^{2+}$ current in CA1 neurons. To minimize the inactivation of the $Ca^{2+}$ channel during recording, $CaCl_2$ was replaced with $BaCl_2$ having the same molar number in the recording solution (Budde et al., 2002). Short depolarization of 50 ms from −90 mV to −10 mv in the presence of $Na^+$ channel blocker tetrodotoxin produced large inward $Ba^{2+}$ current in CA1 neurons (FIG. 6A to FIG. 6C). This $Ba^{2+}$ current mediated by the $Ca^{2+}$ channel in the control solution was initially constant. Then, after 10 minutes, this $Ba^{2+}$ current gradually decreased due to a repetition of depolarization (2-minute interval) (FIG. 6A). However, SYR (100 μM) rapidly reduced the $Ba^{2+}$ current. As a result, subsequent continuous depolarization accelerated the reduction of $Ca^{2+}$ channel current. Statistical analysis showed a significant correlation between time and treatment in terms of peak amplitude of $Ca^{2+}$ channel current ($F_{(1, 16)}$=28.84, p<0.001, two-way ANOVA with a post hoc Tukeys HSD test).

Figure 6D:
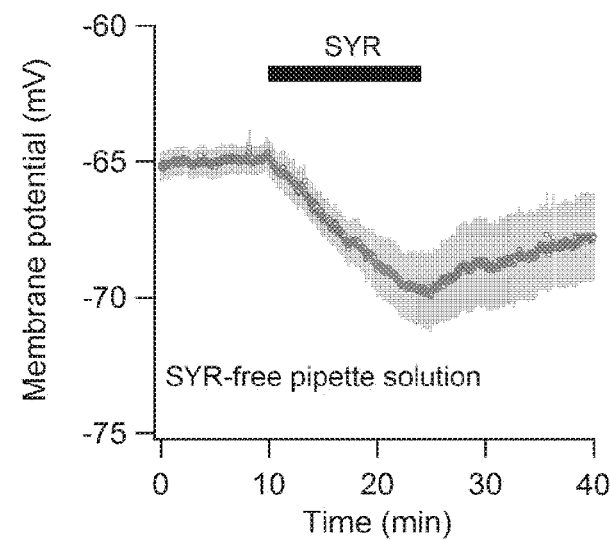
FIG. 6D and FIG. 6E show respectively the effects of SYR (100 μM) applied to the extracellular fluid on the CA1 neuronal membrane potential under the condition (D) that SYR is absent in the pipette solution and under the condition (E) that SYR is present in the pipette solution.
Figure 6E:
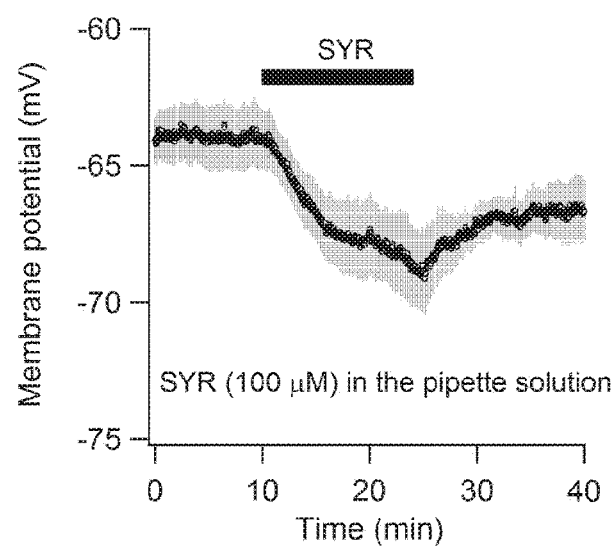
Figure 6F:
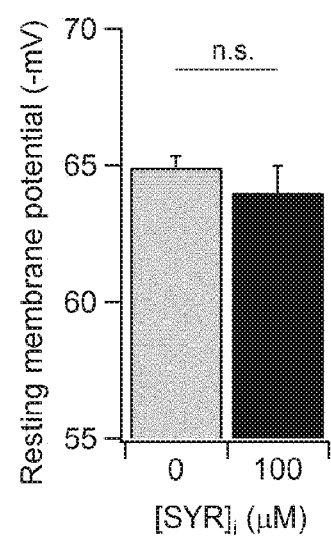
FIG. 6F and FIG. 6G show respectively the resting membrane potential (F) and the degree of hyperpolarization (G) caused by SYR under the condition that SYR is absent in the pipette solution and under the condition that SYR is present in the pipette solution [n=9 cells (SYR-free pipette solution) and n=4 cells (100 microM SYR-containing pipette solution)].
Figure 6G:
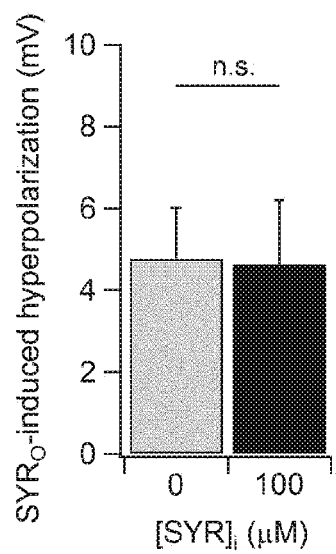

Next, whole-cell current clamp recordings were used to check the effect of SYR on the membrane potential of CA1 neurons. Significant hyperpolarization was observed in CA1 neurons in response to SYR application (FIG. 6D). This hyperpolarization seems to be due to extracellular SYR, since SYR (100 μM) in the pipette solution did not affect resting membrane potential (t=−1.03, p>0.05; FIG. 6F). In addition, the application of the bath containing SYR resulted in a hyperpolarization similar to that measured with a pipette solution containing SYR in CA1 neurons (FIG. 6G). These results suggest that SYR reduces $Ca^{2+}$ influx and hyperpolarizes the resting membrane potential of the neuron.

Experimental Example 7

Checking of Inhibition of Epilepsy Activity of Hippocampal CA1 Region by SYR

Figure 7A:
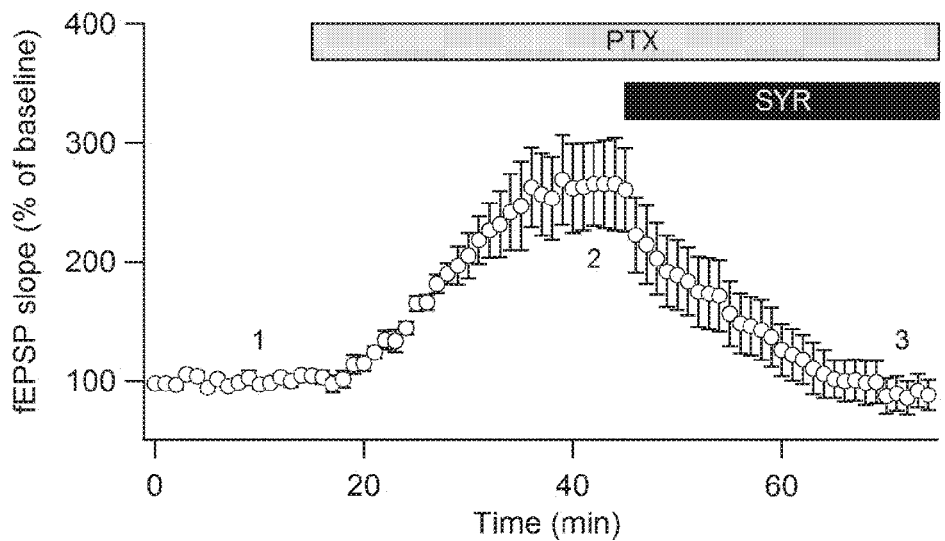
FIG. 7A shows the first slope of fEPSP measured in CA1 over time as a percentage relative to that of the baseline.
Figure 7B:
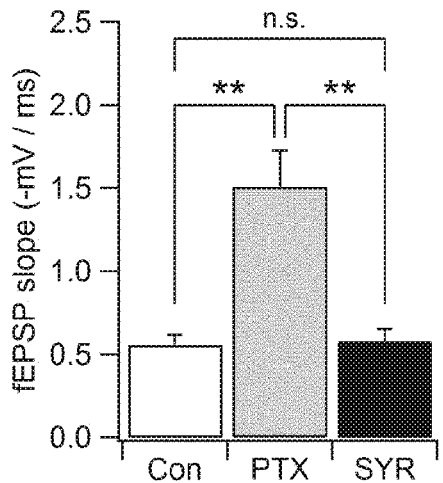
FIG. 7B summarizes the mean slope of fEPSP measured over each of the baseline (Con, 10 to 15 mins), picrotoxin perfusion (PTX, 40 to 45 mins), and SYR perfusion (SYR, 70 to 75 mins) (***p<0.01, $F_{(2,12)}$=2.02, n=5 slices by one-way ANOVA with a Bonferroni post hoc test).
Figure 7C:
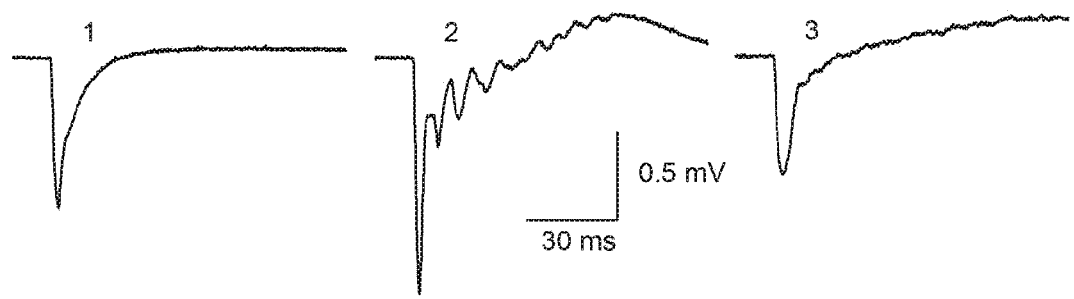
FIG. 7C shows a representative trace of fEPSP and population spike (PS) obtained at a time (1 to 3 mins) indicated in FIG. 7A.
Figure 7D:
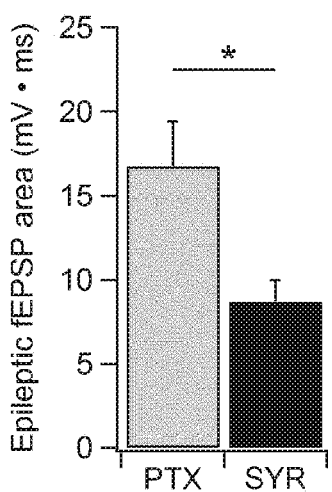
FIGS. 7D and 7E show the effect of SYR on the area (D) of the population spike (PS) region and the amplitude (E) of the first PS during picrotoxin-induced epilepsy activity.
Figure 7E:
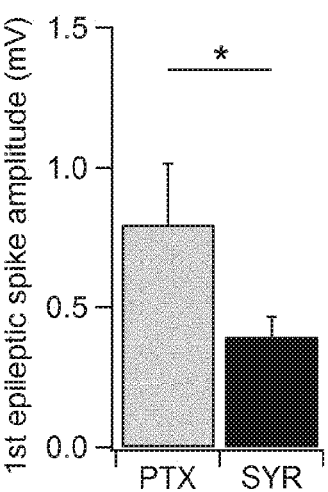

Selective inhibition of excitatory synaptic transmission rather than inhibitory synapse transmission means that SYR may change the balance between synapse excitation and inhibition in neurons. We checked whether this synapse regulation might inhibit epilepsy pathogenic activity caused by excessive excitement of the neural network. To model an epilepsy pathogenic neuron network in experimental conditions (in vitro), the hippocampal slice was prepared while the CA3 region was left. During recording, ACSF containing picrotoxin (50 μM) was perfused in intact hippocampal slices. When replacing normal ACSF with picrotoxin ACSF, the slope of fEPSP measured in the pyramidal cell layer gradually increased (FIG. 7A and FIG. 7B). Continuous picrotoxin perfusion (>20 min) discharged an epilepsy pathogenic excitation wave. This wave was characterized by a three to seven population spikes (PS) waveform of a decreasing amplitude (FIG. 7C). The slope of fEPSP was rapidly reduced by application of the SYR containing bath in the epilepsy-induced hippocampal slice as in the slope reduction of fEPSP in the normal slice by SYR (FIG. 7A to FIG. 7C). Thus, the epilepsy pathological excitation wave was significantly inhibited by SYR. As the slope of fEPSP was rapidly reduced by SYR, an area of the epilepsy pathological fEPSP (n=5 slices, t=2.7, p<0.05, Student's t-test) and an amplitude of a first epilepsy pathological excitation wave (t=2.51, p<0.05, Student's t-test) decreased during SYR perfusion (FIG. 7D and FIG. 7E). These results indicate that excitatory pre-synaptic inhibition by SYR attenuates epilepsy pathological activity in the hippocampus.

Example 8

Behavioral Analysis

In an open field test, we video-recorded a movement of a 7 to 10-week-old mouse in a white plastic chamber (40×

40×40 cm) in a darkened room for 30 minutes. Then, the moving distance of the mouse was measured using Ethovision XT (Noldus) software.

Figure 8:
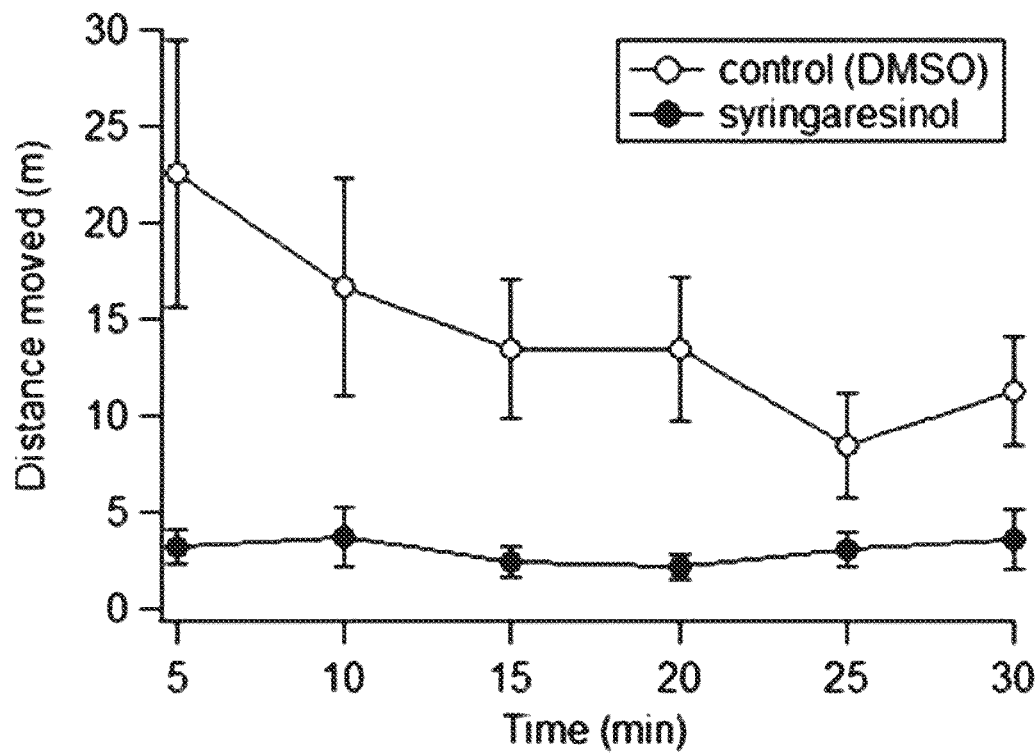
FIG. 8 shows the change in the activity of the mouse by syringaresinol.
Figure 8:
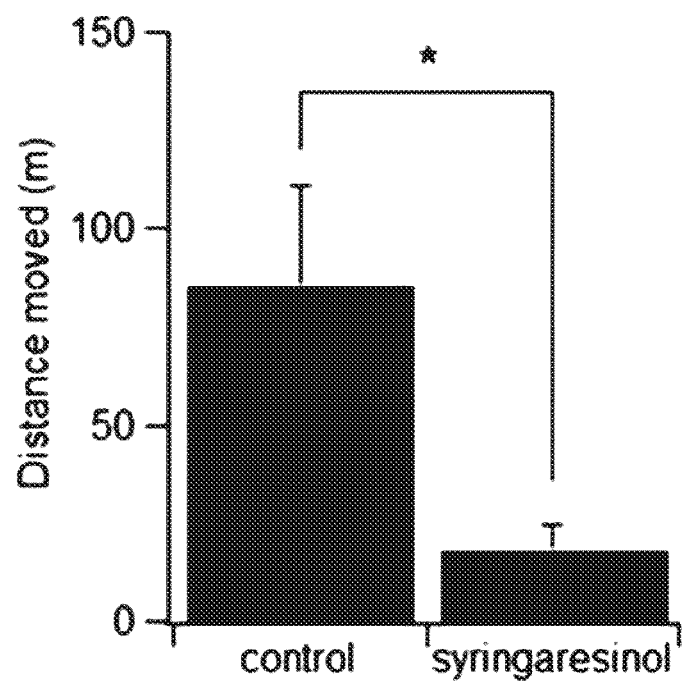

To determine the change of the activity of the mice by syringaresinol, we injected syringaresinol at a concentration of 10 mg/kg intraperitoneally into the mice. After 30 minutes, we measured the activity of the mice via an open field test. The results are shown in FIG. 8. In this connection, control was injected with DMSO, a solvent used for dissolving syringaresinol. The open field test was conducted for 30 minutes. The activity of the mouse was checked at a 5-minute interval. Further, during the 30-minute test, the total movement distance of the mouse was measured.

As shown in FIG. 8, syringaresinol (10 mg/kg) reduced the activity of the mouse to ¼ of the activity of the mouse of the control. This suggests that syringaresinol may be an effective remedy for hyperactivity-related diseases such as hyperactivity-based attention deficit disorder or autism.

The invention claimed is:

1. A method for treating a neurological disease or mental disease comprising administering an effective amount of a compound represented by a following Chemical Formula 1 into an individual in need thereof:

[Chemical Formula 1]

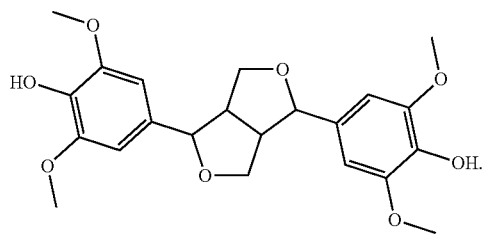

2. The method of claim 1, wherein the neurological disease or mental disease is caused by synaptic excitation-inhibition imbalance.

3. The method of claim 2, wherein the neurological disease includes one selected from a group consisting of brain tumor, cerebral infarction, hypertensive cerebral hemorrhage, cerebral contusion, cerebral arteriovenous malformation, brain abscess, encephalitis, hydrocephalus, epilepsy, concussion, cerebral palsy, dementia, spinal cord tumor, spinal arteriovenous malformation, spinal cord infarction, pain, brain pain, and migraine.

4. The method of claim 2, wherein the mental disease includes one selected from a group consisting of hyperactivity, attention deficit, autism, posttraumatic stress disorder (PTSD), intelligence disorder, dementia, drug addiction, schizophrenia, obsessive-compulsive disorder, delusion of grandeur, character disorder, neuropathy, alcoholism, enuresis, manic depression and motor function disorder.

5. A method for controlling an excitatory synaptic transmission comprising administering an effective amount of a comprising a compound represented by a following Chemical Formula 1 into an individual in need thereof:

[Chemical Formula 1]

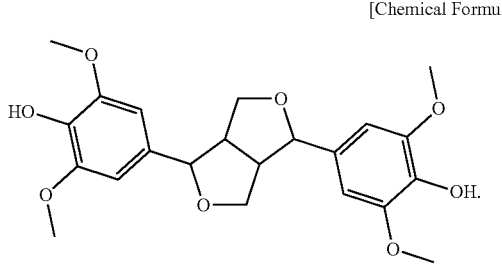

* * * * *